United States Patent
Betourne et al.

(10) Patent No.: US 10,322,114 B2
(45) Date of Patent: Jun. 18, 2019

(54) FORMULATION OF A RILUZOLE SOLUTION WITH BETA-CYCLODEXTRINS

(71) Applicants: Above and Beyond NB LLC, New York, NY (US); Emory University, Atlanta, GA (US)

(72) Inventors: Alexandre Betourne, Atlanta, GA (US); Nicholas M Boulis, Atlanta, GA (US); Raymond T Bartus, San Diego, CA (US)

(73) Assignees: Above and Beyond NB, LLC, New York, NY (US); Emory University, Atlanta, GA (US)

( * ) Notice: Subject to any disclaimer, the term of this patent is extended or adjusted under 35 U.S.C. 154(b) by 0 days.

(21) Appl. No.: 15/664,937

(22) Filed: Jul. 31, 2017

(65) Prior Publication Data
US 2019/0030007 A1    Jan. 31, 2019

(51) Int. Cl.
A61K 31/428    (2006.01)
A61K 9/00    (2006.01)
A61K 9/08    (2006.01)
A61K 47/40    (2006.01)

(52) U.S. Cl.
CPC .......... *A61K 31/428* (2013.01); *A61K 9/0053* (2013.01); *A61K 9/0085* (2013.01); *A61K 9/08* (2013.01); *A61K 47/40* (2013.01)

(58) Field of Classification Search
CPC .... A61K 31/428; A61K 47/40; A61K 9/0085; A61K 9/0053; A61K 9/08
See application file for complete search history.

(56) References Cited

U.S. PATENT DOCUMENTS

| 5,527,814 A | 6/1996 | Louvel |
| 5,674,885 A | 10/1997 | Boireau et al. |
| 9,200,088 B2 | 12/2015 | Antle |
| 2015/0010549 A1 | 1/2015 | Gjorstrup |

FOREIGN PATENT DOCUMENTS

WO    1994013288 A1    6/1994

OTHER PUBLICATIONS

Carlos Zarate (Expert Opin Drug Metab Toxicol. Sep. 2008 ; 4(9): 1223-1234) (Year: 2008).*
Li J, Sung M, Rutkove SB (2013) Electrophysiologic Biomarkers for Assessing Disease Progression and the Effect of Riluzole in SOD1 G93A ALS Mice. PLoS ONE 8(6): (Year: 2013).*
Detailed pharmacology review of neuroprotective agents for ALS Traynor BJ et al. 2005 (Year: 2005).*
Guiterrez et al., "Development of Intrathecal Riluzole: A New Route of Administration for the Treatment of Amyotrophic Lateral Sclerosis Patients," Neurosurgery, 2016, pp. 193, vol. 63.
Wang et al, "Characterization and evaluation of synthetic riluzole with β-cyclodextrin and 2,6-di-O-methyl-β-cyclodextrin inclusion complexes," Carbohydrate Polymers, 2015, pp. 9-16, vol. 129.

* cited by examiner

*Primary Examiner* — Angela C Brown-Pettigrew
(74) *Attorney, Agent, or Firm* — Polsinelli PC

(57) ABSTRACT

The present invention provides methods for parenterally administering riluzole to subjects in need of treatment.

19 Claims, 16 Drawing Sheets
(7 of 16 Drawing Sheet(s) Filed in Color)

FORMULATION OF A RILUZOLE SOLUTION WITH BETA-CYCLODEXTRINS

FIELD OF THE INVENTION

The present invention provides methods for parenterally administering riluzole to subjects in need of treatment.

BACKGROUND OF THE INVENTION

Riluzole, an active pharmaceutical ingredient that has a very low solubility in water (i.e., about 0.3 mg/mL at neutral pH), is used to treat amyotrophic lateral sclerosis (ALS). Currently, the only FDA-approved dosage form of riluzole is an oral tablet, which is usually administered at a dose of 50 mg every 12 hours to delay the onset of ventilator-dependence or tracheostomy. An increased rate of adverse events including dizziness, diarrhea, and anorexia prevent higher doses of riluzole from being administered orally. Accordingly, there remains a need in the art for alternative treatment regimens that have an improved safety profile.

BRIEF DESCRIPTION OF THE FIGURES

The patent or application file contains at least one drawing executed in color. Copies of this patent or patent application with color drawing(s) will be provided by the Office by request and payment of the necessary fee.

An appropriate amount of riluzole was added to aqueous solutions that contained 10%, 5%, 2.5%, 1%, 0.5%, 0.25%, and 0.1% HP-β-CD, all made isotonic with NaCl, to aqueous NaCl solution (9 mg/ml NaCl, normal saline), and to pure water. An appropriate excess amount of riluzole was added to each of the sample solution as needed to obtain saturated solutions of riluzole for HPLC analysis of Riluzole concentration, and to perform XRPD analysis on undissolved solid riluzole. Riluzole-containing sample suspensions were stirred at 500 rpm at room temperature. Supernatants were assayed after 1 week of equilibration by HPLC for Riluzole concentration, and undissolved solid by XRPD for crystallinity and polymorphism FIG. 3A depicts the XRPD patterns for residual solids recovered from riluzole solubilized in 0.5%, 1%, 2.5%, 5%, and 10% HP-β-CD as well as starting material. FIG. 3B depicts the XRPD patterns for residual solids recovered from riluzole solubilized in 0.1% and 0.25% HP-β-CD as well as water, 9 mg/ml NaCl, and starting material.

FIG. 4A depicts the XRPD patterns for residual solids recovered from riluzole solubilized in 0.5%, 1%, 2.5%, 5%, and 10% HP-β-CD as well as starting material. FIG. 4B depicts the XRPD patterns for residual solids recovered from riluzole solubilized in 0.1% and 0.25% HP-β-CD as well as water, 9 mg/ml NaCl, and starting material.

FIG. 7A depicts the spread of riluzole accumulation in the spinal cord (SC) after 7 days, rostral and caudal to the catheter tip. After 7 days, riluzole accumulated at levels greater than 1000 ng/g from the T4 vertebrae to the T12 vertebrae (white bars). After 14 days, riluzole accumulated at levels greater than 1000 ng/g from the T2 vertebrae to the L2 vertebrae (black bars). FIG. 7B depicts the total amount of riluzole accumulation in the spinal cord after day 7 (white bar), and day 14 (black bar).

FIG. 8A depicts the elimination profile of riluzole from plasma of both dogs. FIG. 8B depicts the elimination profile of riluzole from urine of both dogs.

FIG. 9A depicts the elimination profile of riluzole from plasma of both dogs. FIG. 9B depicts the riluzole concentration remaining in the brain tissue of both dogs after the 96 hours washout. FIG. 9C depicts the riluzole concentration remaining in the spinal cord tissue of both dogs after the 96 hours washout.

FIG. 10A depicts riluzole plasma levels of dogs treated orally (white bars) and dogs treated by IT infusion (black bars). FIG. 10B depicts riluzole urine levels of dogs treated orally (white bars) and dogs treated by IT infusion (black bars). FIG. 10C depicts riluzole CSF levels of dogs treated orally (white bars) and dogs treated by IT infusion (black bars).

FIG. 11A depicts riluzole concentration in brain tissue from dogs treated orally (white bars) and dogs treated by IT infusion (black bars). FIG. 11B depicts riluzole concentration in spinal cord tissue from dogs treated orally (white bars) and dogs treated by IT infusion (black bars).

FIG. 12A is a graph depicting riluzole plasma concentrations following oral riluzole (1.3 mg/kg, bid, for 10 days; grey bar) and combination treatment with oral and IT riluzole (1.7-2 mg/kg, bid+0.20 mg/h, for 5 days; blue bar). FIG. 12B is a graph depicting riluzole spinal cord (SC) concentrations vs. the distance from the catheter tip following oral riluzole (1.3 mg/kg, bid, for 10 days; open circle), IT riluzole (0.25 mg/h for 5 days; closed circle) and combination treatment with oral and IT riluzole (1.7-2 mg/kg, bid+0.20 mg/h, for 5 days; closed square).

SUMMARY OF THE INVENTION

Figure 1:
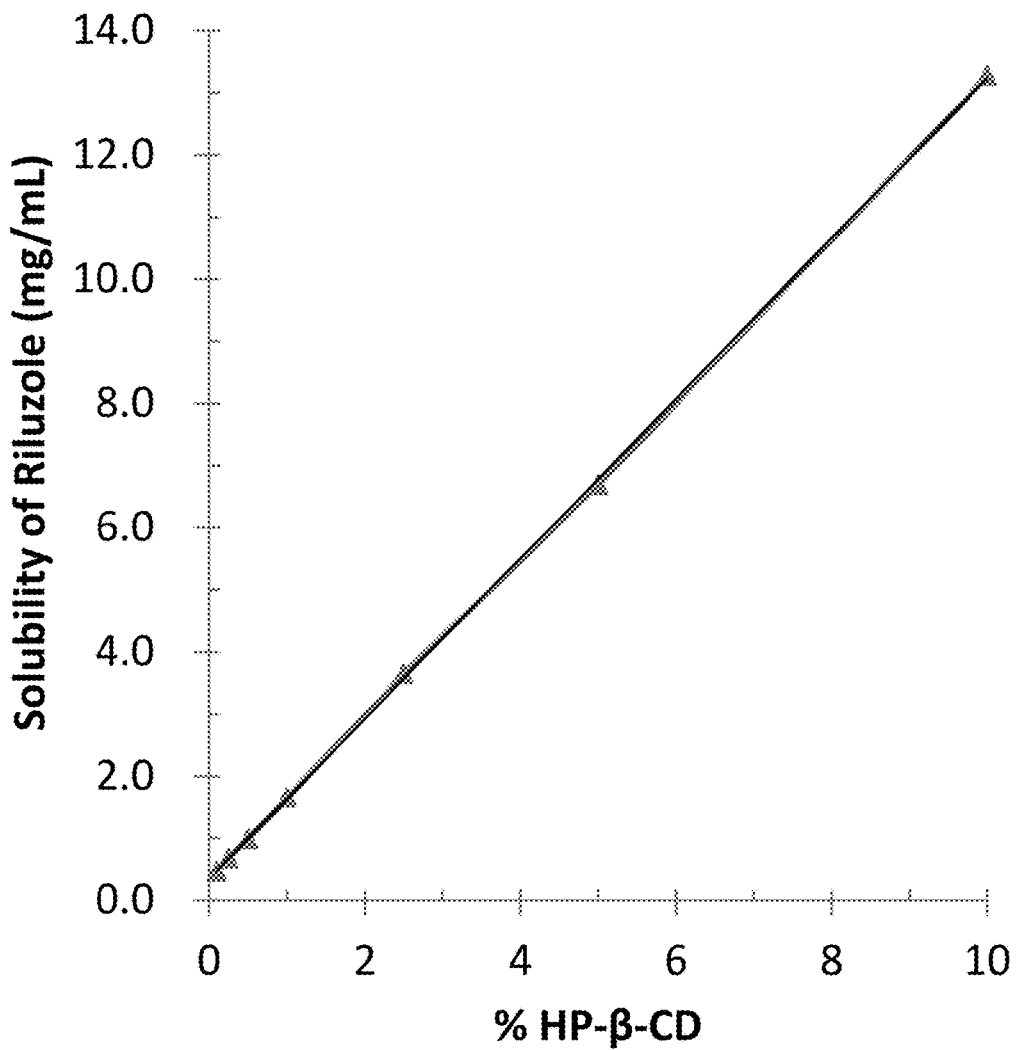
FIG. 1 depicts the solubility of riluzole in hydroxypropyl-beta-cyclodextrin (HP-β-CD) at room temperature after 48 hours. An appropriate amount of riluzole was added to aqueous solutions that contained 10%, 5%, 2.5%, 1%, 0.5%, 0.25%, and 0.1% HP-β-CD, all made isotonic with NaCl, to aqueous NaCl solution (9 mg/ml NaCl, normal saline), and to pure water. An appropriate excess amount of riluzole was added to each of the sample solutions as needed to obtain saturated solutions of riluzole for HPLC analysis of Riluzole concentration, and to perform XRPD analysis on undissolved solid riluzole. Riluzole-containing sample suspensions were stirred at 500 rpm at room temperature. Supernatants were assayed after 48 hours of equilibration by HPLC for Riluzole concentration, and undissolved solid by XRPD for crystallinity and polymorphism.

In an aspect, the present disclosure encompasses a method for treating a subject in need thereof, the method comprising parenterally administering to the subject riluzole at a dose that is less than 10 mg per day.

In another aspect, the present disclosure encompasses a method for treating a subject in need thereof, the method comprising parenterally administering to the subject riluzole at a dose that is about 1 mg to about 9 mg per day.

In an aspect, the present disclosure encompasses a method for treating a subject in need thereof, the method comprising intrathecally administering to the subject riluzole at a dose that is less than 10 mg per day, optionally in combination with an oral dose of riluzole.

In another aspect, the present disclosure encompasses a method for treating a subject in need thereof, the method comprising intrathecally administering to the subject riluzole at a dose that is about 1 mg to about 9 mg per day, optionally in combination with an oral dose of riluzole.

In another aspect, the present disclosure encompasses a method for treating a subject in need thereof, the method comprising intrathecally administering to the subject riluzole at a dose that is about 0.4 mg to about 4 mg per day, optionally in combination with an oral dose of riluzole.

In each of the above aspects, the subject in need of treatment with riluzole may be a subject with motor neuron disease, spinal muscular atrophy, spinal cord injury, Parkinson's disease, Multiple Sclerosis, Alzheimer's disease, depression, Tourette Syndrome, pain, spasticity, general anxiety disorders, schizophrenia, or bipolar disorder.

Other aspects and iterations of the invention are described more thoroughly below.

DETAILED DESCRIPTION

The present disclosure provides pharmaceutical compositions comprising riluzole dissolved in a ß-cyclodextrin solution. In certain embodiments, these compositions also do not contain toxic excipients, or amounts of excipients that would be toxic when the composition is injected or infused into a subject's brain, spinal cord, or a cerebral ventricle. Also provided herein are methods of parenterally administering a pharmaceutical composition comprising riluzole dissolved in a ß-cyclodextrin solution to a subject in need thereof.

(I) Pharmaceutical Compositions

One aspect of the present disclosure provides a pharmaceutical composition comprising riluzole dissolved in a ß-cyclodextrin solution. Preferably, the pharmaceutical composition is iso-osmolar and has a physiological, or close to physiological pH. Detailed below are the components of the compositions and stability properties of the compositions.

(a) Riluzole

Riluzole (2-Amino-6-(trifluoromethoxy)benzothiazole) is a sodium channel-blocking benzothiazole anticonvulsant drug with the following chemical structure:

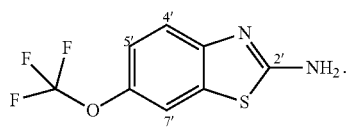

Compositions disclosed herein may contain about 0.01 mg/ml to about 45 mg/ml or riluzole. In some embodiments, compositions may comprise at least about 15 mg/ml of riluzole. For example, a composition may comprise about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, or about 45 mg/ml of riluzole. In some embodiments, compositions may comprise less than about 15 mg/ml of riluzole. For example, a composition may comprise about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or less of riluzole. In certain embodiments, compositions may comprise about 0.1 mg/ml to about 10 mg of riluzole. In certain embodiments, compositions may comprise about 0.4 mg/ml to about 10 mg of riluzole. In certain embodiments, compositions may comprise about 0.1 mg/ml to about 1 mg of riluzole. In certain embodiments, compositions may comprise about 0.4 mg/ml to about 4 mg of riluzole. In certain embodiments, compositions may comprise about 1 mg/ml to about 10 mg of riluzole. In certain embodiments, compositions may comprise about 1 mg/ml to about 5 mg of riluzole.

(b) ß-Cyclodextrin Solution

As used herein, the term "ß-cyclodextrin solution" refers to a solution comprising at least one ß-cyclodextrin derivative, wherein the total amount of ß-cyclodextrin derivative in solution is at least about 1% (w/v). For example, the total amount of ß-cyclodextrin derivative in solution may be about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), or more. These values can also be used to define a range, such as from about 1% (w/v) to about 15% (w/v), about 1% (w/v) to about 10% (w/v), about 1% (w/v) to about 5% (w/v), about 5% (w/v) to about 10% (w/v), or the like. A ß-cyclodextrin solution of the present disclosure may comprise one, two, three, four, five, or more different ß-cyclodextrin derivatives dissolved in an aqueous solvent.

(i) ß-Cyclodextrin

As used herein, the term "ß-cyclodextrin" (ß-CD) refers to a cyclic oligosaccharide having the following structure:

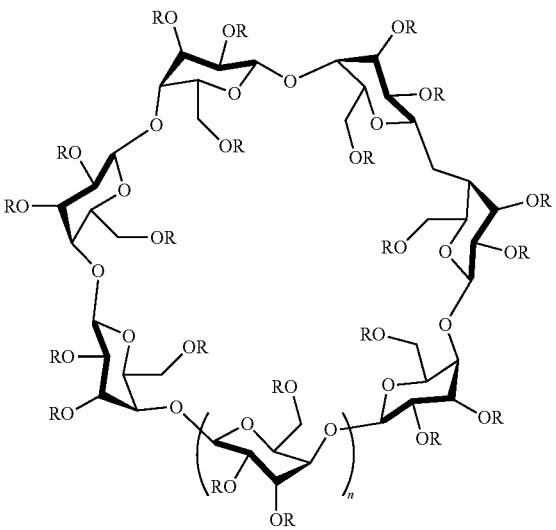

wherein n=1, and R is independently selected from a hydrogen, a hydrocarbon or a substituted hydrocarbyl. The term "parent ß-cyclodextrin" refers to a cyclic oligosaccharide of the above structure, wherein R is hydrogen. The term "ß-cyclodextrin derivative" refers to a cyclic oligosaccharide of the above structure, wherein at least one R is a hydrocarbon or a substituted hydrocarbyl. ß-cyclodextrin derivatives have increased aqueous solubility compared to parent ß-cyclodextrin.

In some embodiments, a ß-cyclodextrin derivative is selected from the group consisting of a sulfobutylether β-CD (SBE-β-CD), a hydroxyethyl-β-CD (HE-β-CD), a hydroxypropyl β-CD (HP-β-CD), a methyl-β-CD (M-β-CD), a dimethyl-β-CD (DM-β-CD), an ethyl-β-CD (E-β-CD), a diethyl-β-CD (DE-β-CD), a carboxymethyl-β-CD (CM-β-CD), a carboxymethyl ethyl-β-CD (CME-β-CD), a tri-O-methyl-β-CD (TRIMEB), a tri-O-ethyl-β-CD (TE-β-CD), tri-O-butyryl-β-CD (TB-β-CD), a tri-O-valeryl-β-CD (TV-β-CD), a di-O-hexanoyl-β-CD (DH-β-CD), a glucosyl-β-CD ($G_1$-β-CD), a maltosyl-β-CD ($G_2$-β-CD), a 2-hydroxy-3-trimethyl-ammoniopropyl-β-CD (HTMAP-β-CD). In other embodiments, a β-cyclodextrin derivative is selected from the group consisting of a sulfobutylether β-CD (SBE-β-CD), a hydroxypropyl β-CD (HP-β-CD), a methyl-β-CD (M-β-CD), a dimethyl-β-CD (DM-β-CD), a carboxymethyl-β-CD (CM-β-CD), a carboxymethyl ethyl-β-CD (CME-β-CD), a 2-hydroxy-3-trimethyl-ammoniopropyl-β-CD (HTMAP-β-CD). It will be appreciated that the degree and pattern of substitution for any β-CD derivative can vary. Further, for any ß-cyclodextrin derivative, substitution of the primary hydroxyl group may occur randomly, and in certain instances resulting in a mixture, or may be site-specific and resulting in a homogenous composition. Nonetheless, a skilled artisan will be able to experimentally determine the influence, if any, these variations have on solubilizing riluzole based on the disclosures herein. In an exemplary embodiment, a ß-cyclodextrin derivative is selected from the group consisting of Trappsol® 2,6-di-O-methyl-ß-cyclodextrin (CTD Holdings), Trappsol® HPBCD-EC (hydroxypropyl β-CD—endotoxin controlled) (CTD Holdings), Trappsol® Cyclo™ (CTD Holdings), randomly methylated Trappsol® (CTD Holdings), Captisol® (Ligand), and Beta Cyclodextrin Sulfobutyl Ethers-Ethyl Ethers, DS 4.5, 4.5 (Ligand).

Methods for making ß-cyclodextrins are well known in the art. For example, parent ß-cyclodextrin can be obtained by hydrolysis of starch using a cyclodextrin glycosyl transferase. Further details may be found throughout the prior art, including, but not limited to, U.S. Pat. Nos. 3,812,011 and 5,118,354. Methyl-ß-cyclodextrins and ethyl-ß-cyclodextrins are generally formed by alkylation of the hydroxyl groups of parent ß-cyclodextrin, while hydroxypropyl-ß-cyclodextrins and hydroxyethyl-ß-cyclodextrins are generally form by hydroxyalkylation of the hydroxyl groups of parent ß-cyclodextrin. Glucosyl-ß-cyclodextrins and maltosyl-ß-cyclodextrins may be formed by substituting the primary hydroxyl groups of parent ß-cyclodextrin with saccharides. Hydroxypropyl-ß-cyclodextrins and hydroxyethyl-ß-cyclodextrins, and their preparation by propylene oxide and ethylene oxide addition to parent ß-cyclodextrin, respectively, are described in a U.S. Pat. No. 3,459,731, which is incorporated herein by reference. For a comprehensive review of cyclodextrins, see "Cyclodextrins and their industrial uses," editor Dominique Duchene, Editions Sante, Paris, 1987. For a more recent overview, see J. Szejtli: Cyclodextrins in drug formulations; Part 1, Pharm. Techn. Int. 3(2), 15-22 (1991); and J. Szejtli: Cyclodextrins in drug formulations: Part II, Pharm. Techn. Int. 3(3), 16-24 (1991).

(ii) Aqueous Solvent

Suitable aqueous solvents include any pharmaceutically acceptable aqueous solvent. In some embodiments, an aqueous solvent is sterile water for injection. In other embodiments, an aqueous solvent is a saline solution. Suitable saline solutions may be about 0.1% (w/v) to about 1% (w/v) sodium chloride. For example, a saline solution may be about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v) sodium chloride. These values can also be used to define a range, such as from about 0.1% (w/v) to about 0.5% (w/v) sodium chloride, about 0.25% (w/v) to about 0.75% (w/v) sodium chloride, or about 0.5% (w/v) to about 1% (w/v) sodium chloride. In yet other embodiments, an aqueous solvent is a dextrose solution. Suitable dextrose solutions may be about 2.5% (w/v) to about 5% (w/v) dextrose. For example, a saline solution may be about 2.5% (w/v), about 3% (w/v), about 3.5% (w/v), about 4% (w/v), about 4.5% (w/v), or about 5% (w/v). These values can also be used to define a range. In yet other embodiments, an aqueous solvent is Ringer's Injection, Lactated Ringer's Injection, or glycerol.

(iii) Concentration of ß-Cyclodextrin Derivative in Solution

The amount of ß-cyclodextrin derivative in solution may vary. In some embodiments, a solution of ß-cyclodextrin comprises at least about 1% (w/v) of ß-cyclodextrin derivative, preferably at least about 2% (w/v) of ß-cyclodextrin derivative, more preferably at least about 4% (w/v) of ß-cyclodextrin derivative. For example, a solution of ß-cyclodextrin may comprise about 1% (w/v), about 1.5% (w/v), about 2% (w/v), about 2.5% (w/v), about 3% (w/v), about 3.5% (w/v), about 4% (w/v) of ß-cyclodextrin derivative, or more. As another example, a solution of ß-cyclodextrin may comprise about 5% (w/v), about 6% (w/v), about 7% (w/v), about 8% (w/v), about 9% (w/v), about 10% (w/v) of ß-cyclodextrin derivative, or more. As another example, a solution of ß-cyclodextrin may comprise about 15% (w/v), about 20% (w/v), about 25% (w/v), about 30% (w/v), about 35% (w/v), about 40% (w/v), about 45% (w/v) of ß-cyclodextrin derivative, or more. These values can also be used to define a range, such as from about 1% (w/v) to about 4% (w/v), about 2% (w/v) to about 4% (w/v), or about 3% (w/v) to about 4% (w/v) ß-cyclodextrin derivative. Methods for making aqueous, ß-cyclodextrin solutions are well known in the art, and are further detailed in the examples.

(c) Additional Components

In some embodiments, compositions of the invention may further comprise one or more pharmaceutically acceptable excipients suitable for parenteral administration and/or one or more additional active ingredients. Non-limiting examples of excipients include preservatives (e.g. antimicrobials, antioxidants, etc.), pH modifiers and buffers, chelating agents, antimicrobial agents, tonicity-adjusting agents, and combinations of any of these agents. The choice of suitable excipients will be influenced, in part, by the intended route of administration. Compositions formulated to be administered as a bolus in the intrathecal space typically will contain fewer, if any, preservatives, pH modifiers and buffers, chelating agents, antimicrobial agents, or tonicity-adjusting agents.

Non-limiting examples of preservatives include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-carotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)- mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof. In an exemplary embodiment, the preservatives are an antioxidant, such as a-tocopherol or ascorbate, and antimicrobials, such as parabens, chlorobutanol or phenol.

Non-limiting examples of pH modifiers and buffers may include citric acid, acetic acid, tartaric acid, malic acid, fumaric acid, hydrochloric acid, lactic acid, phosphoric acid, sorbic acid, succinic acid, benzoic acid, sodium acetate, sodium borate, sodium carbonate, sodium bicarbonate, sodium phosphate, potassium phosphate, sodium hydroxide, maleic acid, sodium citrate, and sodium tartrate.

A chelating agent may be included as an excipient to immobilize oxidative groups, including but not limited to metal ions, in order to inhibit the oxidative degradation of the riluzole by these oxidative groups. Non-limiting examples of chelating agents include lysine, methionine, glycine, gluconate, polysaccharides, glutamate, aspartate, disodium ethylenediaminetetraacetate ($Na_2EDTA$), calcium disodium ethylenediaminetetraacetate, and (tri)sodium citrate.

An antimicrobial agent may be included as an excipient to minimize the degradation of the compound according to this disclosure by microbial agents, including but not limited to bacteria and fungi. Non-limiting examples of antimicrobials include parabens, chlorobutanol, phenol, calcium propionate, sodium nitrate, sodium nitrite, sorbic acid, $Na_2EDTA$, and sulfites including but not limited to sulfur dioxide, sodium bisulfite, and potassium hydrogen sulfite.

Non-limiting examples of tonicity agents include, but are not limited to, mannitol, dextrose, sodium chloride, sorbitol, sucrose, lactose, and glycerol.

(d) pH

The pH of a pharmaceutical composition of the present disclosure will be influenced, in part, by the intended route of administration. Compositions formulated to be administered as a bolus in the intrathecal space may have a pH between about 3 to about 8. Compositions formulated to be administered intravenously may have a pH between about 3 to about 10.5. In some embodiments, the pH is about 3, about 3.5, about 4, about 4.5, about 5, about 5.5, about 6, about 6.5, about 7, about 7.5 about 8, about 8.5, of about 9. In other embodiments, the pH is between about 4 and about 8, or between about 5 and about 8, or between about 6 and about 8. In still other embodiments, the pH is between about 4.5 and about 8, or between about 4.5 and about 7.5. In yet other embodiments, the pH is between about 5 and about 7.5, or between about 5.5 and about 8. In alternative embodiments, the pH is between about 5.5 and about 7.5. The pH of a pharmaceutical composition may be adjusted with acids or bases such as hydrochloric acid or sodium hydroxide, or by the addition of a pH modifier, as described above.

(e) Osmolarity

Compositions of the present invention have an osmolarity suitable for parenteral administration. For example, compositions of the present invention can have an osmolarity of about 200 mOsmole to about 400 mOsmole. In certain embodiments, osmolarity may be about 200 mOsmole to about 370 mOsmole, more preferably about 240 mOsmole to about 330 mOsmole, even more preferably about 260 mOsmole to about 310 mOsmole.

(f) Stability of the Compositions

Pharmaceutical compositions of the present disclosure are sufficiently stable. As used herein, the phrase "stable" refers to riluzole content in a solution over a specified period of time and at a given temperature, with no more than about 15% loss as compared to time zero. When the riluzole content is maintained over the specified period of time (i.e. the loss is not more than 15%, or preferably 10%), the solution is a "stable" riluzole formulation or riluzole solution. Any suitable method for measuring the concentration of riluzole in solution may be used.

In some embodiments, the solution is stable for at least 1 week, at least 2 weeks, at least 3 weeks, or at least 4 weeks when stored at about 2° C. to about 8° C. In other embodiments, the solution is stable for at least 1 month, at least 2 months, at least 3 months, or at least 4 months when stored at about 2° C. to about 8° C. In other embodiments, the solution is stable for at least 5 months, at least 6 months, at least 7 months, or at least 8 months when stored at about 2° C. to about 8° C. In other embodiments, the solution is stable for at least 9 months, at least 10 months, at least 11 months, or at least 12 months when stored at about 2° C. to about 8° C.

In some embodiments, the solution is stable for at least 1 week, at least 2 weeks, at least 3 weeks, or at least 4 weeks when stored at room temperature. In other embodiments, the solution is stable for at least 1 month, at least 2 months, at least 3 months, or at least 4 months when stored at room temperature. In other embodiments, the solution is stable for at least 5 months, at least 6 months, at least 7 months, or at least 8 months when stored at room temperature. In other embodiments, the solution is stable for at least 9 months, at least 10 months, at least 11 months, or at least 12 months when stored at room temperature.

In some embodiments, the solution is stable for at least 1 week, at least 2 weeks, at least 3 weeks, or at least 4 weeks when stored at about 37° C. In other embodiments, the solution is stable for at least 1 month, at least 2 months, at least 3 months, or at least 4 months when stored at about 37° C. In other embodiments, the solution is stable for at least 5 months, at least 6 months, at least 7 months, or at least 8 months when stored at about 37° C. In other embodiments, the solution is stable for at least 9 months, at least 10 months, at least 11 months, or at least 12 months when stored at about 37° C.

In some embodiments, the solution is stable for at least 1 week, at least 2 weeks, at least 3 weeks, or at least 4 weeks when stored at about 40° C. In other embodiments, the solution is stable for at least 1 month, at least 2 months, at least 3 months, or at least 4 months when stored at about 40° C. In other embodiments, the solution is stable for at least 5 months, at least 6 months, at least 7 months, or at least 8 months when stored at about 40° C. In other embodiments, the solution is stable for at least 9 months, at least 10 months, at least 11 months, or at least 12 months when stored at about 40° C.

(g) Formulation of the compositions for administration

Compositions provided herein are preferably formulated for parenteral administration. The term "parenteral," as used herein, includes subcutaneous, intravenous, intra-arterial, intramuscular, intrathecal, intra-articular, or intrasternal injection, or infusion techniques. Compositions provided herein may be packaged as single dose units (e.g. ampoules, pre-filled disposable syringes, vials,) or multiple dose units in volumes suitable for the route of administration. Alternatively, compositions provided herein may be packaged as an infusion solution, or a lyophilized powder for reconstitution. Formulation of pharmaceutical compositions is discussed in, for example, Hoover, John E., Remington's Pharmaceutical Sciences, Mack Publishing Co., Easton, Pa.

(1975), and Liberman, H. A. and Lachman, L., Eds., Pharmaceutical Dosage Forms, Marcel Decker, New York, N.Y. (1980). In an exemplary embodiment, compositions provided herein are formulated for intrathecal administration.

Briefly, compositions provided herein can be formulated by dissolving ß-cyclodextrin in an aqueous solvent; adding an amount of riluzole to obtain a desired concentration of riluzole and mixing until the riluzole is dissolved; and adjusting the pH as needed. Each of the above steps may occur at room temperature, or at a temperature with a range of about ±20° F. of room temperature. The final composition may be filter sterilized, or sterilized by other methods known in the art.

(h) Preferred Embodiments

In certain embodiments, a pharmaceutical composition of the present disclosure (a) comprises about 0.1 mg per ml to less than 10 mg per ml of riluzole dissolved in a solution comprising at least 1% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients and/or one or more pharmaceutically acceptable excipients. In preferred embodiments, the ß-cyclodextrin is selected from the group consisting of 2,6-di-O-methyl-β-cyclodextrin, 2-hydroxypropyl-ß-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) consists of about 0.1 mg per ml to about 10 mg per ml of riluzole, and optionally one or more pharmaceutically acceptable excipients, dissolved in a solution of at least 1% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients. In preferred embodiments, the ß-cyclodextrin is selected from the group consisting of 2,6-di-O-methyl-β-cyclodextrin, 2-hydroxypropyl-ß-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) comprises about 0.4 mg per ml to about 4 mg per ml of riluzole dissolved in a solution comprising at least 1% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients and/or one or more pharmaceutically acceptable excipients. In preferred embodiments, the ß-cyclodextrin is selected from the group consisting of 2,6-di-O-methyl-β-cyclodextrin, 2-hydroxypropyl-β-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) consists of about 0.4 mg per ml to about 4 mg per ml of riluzole, and optionally one or more pharmaceutically acceptable excipients, dissolved in a solution of at least 1% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients. In preferred embodiments, the ß-cyclodextrin is selected from the group consisting of 2,6-di-O-methyl-β-cyclodextrin, 2-hydroxypropyl-β-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) comprises about 0.1 mg per ml to about 10 mg per ml of riluzole dissolved in a solution comprising about 1% to about 10% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients and/or one or more pharmaceutically acceptable excipients. In preferred embodiments, the ß-cyclodextrin is selected from the group consisting of 2,6-di-O-methyl-β-cyclodextrin, 2-hydroxypropyl-β-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) consists of 0.1 mg per ml to about 10 mg per ml of riluzole, and optionally one or more pharmaceutically acceptable excipients, dissolved in a solution of about 1% to about 15% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients. In preferred embodiments, the ß-cyclodextrin is selected from the group consisting of 2,6-di-O-methyl-β-cyclodextrin, 2-hydroxypropyl-β-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) comprises about 0.4 mg per ml to about 4 mg per ml of riluzole dissolved in a solution comprising about 0.4% to about 4% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients and/or one or more pharmaceutically acceptable excipients. In preferred embodiments, the ß-cyclodextrin is selected from the group consisting of 2,6-di-O-methyl-β-cyclodextrin, 2-hydroxypropyl-β-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) consists of about 0.4 mg per ml to about 4 mg per ml of riluzole, and optionally one or more pharmaceutically acceptable excipients, dissolved in a solution of about 0.4% to about 4% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients. In preferred embodiments, the ß-cyclodextrin is selected from the group consisting of 2,6-di-O-methyl-β-cyclodextrin, 2-hydroxypropyl-β-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) comprises about 1 mg per ml to about 5 mg per ml of riluzole dissolved in a solution comprising about 1% to about 5% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients and/or one or more pharmaceutically acceptable excipients. In preferred embodiments, the ß-cyclodextrin is selected from the group consisting of 2,6-di-O-methyl-β-cyclodextrin, 2-hydroxypropyl-β-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-β-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

In certain embodiments, a pharmaceutical composition of the present disclosure (a) consists of about 1 mg per ml to about 5 mg per ml of riluzole, and optionally one or more pharmaceutically acceptable excipients, dissolved in a solution of about 1% to about 5% (w/v) ß-cyclodextrin and an aqueous solvent; (b) has a pH of about 2.5 to about 8, more preferably a pH of about 5 to about 8, even more preferably a pH of about 7 to about 8; (c) has an osmolarity of about 200 mOsmole to about 400 mOsmole; and (d) is optionally formulated for intrathecal administration. The pharmaceutical composition may further comprise one or more additional active ingredients. In preferred embodiments, the ß-cyclodextrin is selected from the group consisting of 2,6-di-O-methyl-β-cyclodextrin, 2-hydroxypropyl-β-cyclodextrin, and sulfobutylether β-cyclodextrin, and the aqueous solvent is sterile water for injection or sterile saline for injection. In exemplary embodiments, the ß-cyclodextrin is selected from the group consisting of Trappsol® 2,6-di-O-methyl-ß-cyclodextrin (CTD Holdings), Trappsol® HPBCD-EC (CTD Holdings), Trappsol® Cyclo™ (CTD Holdings), Captisol® (Ligand), and Beta Cyclodextrin Sulfobutyl Ethers-Ethyl Ethers, DS 4.5, 4.5 (Ligand).

(II) Methods for Administering the Compositions

The present disclosure provides methods for treating a subject in need thereof by parenterally administering riluzole at a dose that is less than 10 mg per day. Bolus administration and continuous administration are possible. Riluzole may be administered alone or in combination with one or more additional active ingredients. In preferred embodiments, riluzole is formulated as a composition of Section I.

In some embodiments, riluzole is administered into the subject's brain, spinal cord, or a cerebral ventricle. In preferred embodiments, riluzole is intrathecally administered. In each of the above embodiments, the daily dose may be less than 10 mg, less than 9 mg, less than 8 mg, less than 7 mg, less than 6 mg, or less than 5 mg. Alternatively, the daily dose may be less than 4 mg, less than 3 mg, less than 2 mg or less than 1 mg.

In embodiments where riluzole is intrathecally administered or administered into a subject's brain, spinal cord, or a cerebral ventricle, continuous administration is preferred. For example, riluzole may be administered continuously by a pump at a dose that is less than 10 mg every 24 hours, more particularly for example, at a dose that is about 0.4 mg or greater but less than 10 mg every 24 hours. In certain embodiments, the dose may be about 0.4 mg to about 4 mg every 24 hours, about 0.1 mg to about 4 mg every 24 hours, or 1 mg to about 4 mg every 24 hours. In other embodiments, the dose may be about 0.1 mg to less than 10 mg every 24 hours, about 0.1 mg to about 9 mg every 24 hours, about 1 mg to about 9 mg every 24 hours, or about 4 mg to about 9 mg every 24 hours. Administration can continue for, typically, at least about one day and may continue for about 12 months or longer as necessary to treat the subject. Those of skill in the art will appreciate that the infusion rate (i.e. ml/day of a riluzole composition) needed to achieve the above dose will vary depending upon the riluzole concentration in the pharmaceutical composition that is being administered.

Administration can continue for about 1 day, 2 days, 3 days, 4 days, 5 days, 6 days, one week, two weeks, three weeks, one month, two months, three months, six months, nine months, twelve months, or more. In some instances, the dose of riluzole escalates over the course of the therapy. For example, patients may begin therapy at about 0.4 mg/day, and may be increased to about 1 mg/day, about 4 mg/day, or even higher over the course of treatment.

Alternatively, intrathecal administration of riluzole can be interrupted by one or more drug holidays. For example, treatment may be carried out by repeating an administration period and a drug holiday period. The administration period and the drug holiday may be of equal or varying duration. For example, riluzole may be intrathecally administered for about 1 day, 2 days, 3 days, 4 days, 5 days, 6 days, one week, two weeks, three weeks, or four weeks followed by a drug holiday period of about 1 day, 2 days, 3 days, 4 days, 5 days, 6 days, one week, two weeks, three weeks, or four weeks. Each repetition (or cycle) of treatment may be the same, or the treatment period and/or drug holiday period may vary between cycles. The number of repetitions is not particularly limited, as long as it is two or more.

It has also been surprisingly discovered that a combination of orally administered riluzole and intrathecally administered riluzole is safe and does not substantially increase peripheral exposure in comparison with intrathecal administration only. Peripheral exposure may be measured by any method known in the art including, but not limited to, the concentration of riluzole (or a metabolite) measured in a biological sample (e.g. serum, urine, etc.) or serum AUC for riluzole (or a metabolite). Accordingly, in each of the above embodiments, a subject may also be administered an oral dose of riluzole that does not exceed the maximal, oral daily dose (e.g., 100 mg per day or 50 mg BID).

As used herein, the terms "treat," "treating," or "treatment" refer to both therapeutic treatment and prophylactic or preventative measures, wherein the object is to prevent or slow down (lessen) an undesired physiological change or disease/disorder as compared to an untreated subject. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment.

Subjects in need of treatment include those already with the disease, condition, or disorder as well as those prone to have the disease, condition or disorder or those in which the disease, condition or disorder is to be prevented. Preferred subjects are mammals, more preferably humans.

In some embodiments, the present disclosure provides a method for treating a subject with motor neuron disease (MND), preferably amyotrophic lateral sclerosis (ALS). Examples of the symptoms caused by MND include clinical symptoms such as a decrease in respiratory function, spoken language disorder, dysphagia, or limb movement disorder. Treatment of MND may include, but is not limited to, improving a symptom of MND, extending survival of the subject, extending time to tracheostomy of the subject, slowing the rate of functional decline of the subject, or any combination thereof.

In some embodiments, a subject in need thereof is a subject with spinal muscular atrophy. Treatment of spinal muscular atrophy may include, but is not limited to, extending survival of the subject, extending time to tracheostomy of the subject, slowing the rate of functional decline of the subject, or any combination thereof.

In other embodiments, a subject in need thereof is a subject with Parkinson's disease. Treatment of Parkinson's disease may include, but is not limited to, extending survival of the subject, slowing the rate of functional decline of the subject, or any combination thereof.

In other embodiments, a subject in need thereof is a subject with Multiple Sclerosis. Treatment of Multiple Sclerosis may include, but is not limited to, neuroprotection (e.g., slowing the rate of brain volume loss, brain volume change, demyelination, functional decline, etc., or any combination thereof).

In other embodiments, a subject in need thereof is a subject with traumatic or non-traumatic spinal cord injury. Traumatic spinal cord injury results from mechanical disruption of the spinal cord tissue. Non-traumatic spinal cord injury results from a variety of disorders including, but not limited to, spondylosis, tumors and infection. Treatment of a spinal cord injury may include, but is not limited to, improvements in overall neurologic recovery, sensory recovery, functional outcomes, quality of life outcomes, health utilities, as well a decrease in mortality, or any combination thereof.

In other embodiments, a subject in need thereof is a subject with Alzheimer's disease. Treatment of Alzheimer's disease may include, but is not limited to, improving cognitive function or slowing the rate of functional decline (e.g., as measured by standard tests known in the art), reducing glutamate levels in the brain, improving pathological biomarkers (e.g., amyloid beta plaques, levels of tau, phospho-tau, or various amyloid beta peptides, etc.), or any combination thereof.

In other embodiments, a subject in need thereof is a subject with pain or spasticity, and treating reduces the severity, duration and/or frequency of the pain or spasticity.

In other embodiments, a subject in need thereof is a subject with a psychiatric disorder such as depression, Tourette Syndrome, general anxiety disorders, schizophrenia, bipolar disorder, and treating improves a clinical symptom diagnostic of the psychiatric disorder.

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "about," as used herein, refers to ±10%. For example, "about" includes ±10%, ±9%, ±8%, ±7%, ±6%, ±5%, ±4%, ±3%, ±2%, and ±1%.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to a compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The term "parenteral," as used herein, includes subcutaneous, intravenous, intra-arterial, intramuscular, intrathecal, or intrasternal injection, or infusion techniques.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that changes may be made in the specific embodiments that are disclosed and still obtain a like or similar result without departing from the spirit and scope of the invention. Therefore, all matter set forth or shown in the accompanying drawings is to be interpreted as illustrative and not in a limiting sense.

EXAMPLES

The following examples illustrate various iterations of the invention.

Example 1. Studies of Riluzole

Solubility.

To test the solubility of riluzole in hydroxypropyl-beta-cyclodextrin (HP-β-CD), stock solutions were first prepared where stock solution A contained 50 ml of 10% (100 mg/ml) HP-β-CD and 5.5 mg/ml NaCl in $H_2O$ and stock solution B contained 9 mg/ml NaCl in $H_2O$. Stock solutions were used to prepare the following sample solutions for testing (all isotonic with NaCl): 10%, 5%, 2.5%, 1%, 0.5%, 0.25%, and 0.1% HP-β-CD. Solubility was also determined in stock solution B (9 mg/ml NaCl) and in pure $H_2O$. An appropriate excess amount of riluzole was added to each of the sample solution as needed to obtain a saturated solution of riluzole for determination of concentration in the supernatant (equilibrium solubility) by HPLC, and to perform X-Ray powder diffraction (XRPD) on the undissolved riluzole. Riluzole-containing sample solutions were stirred at 500 rpm and allowed to equilibrate at room temperature. (Saturated) solutions of Riluzole were separated from the undissolved solid Riluzole after 48 hours and after 1 week of equilibration. Solutions were analyzed for Riluzole concentration by HPLC to obtain equilibrium solubility of riluzole. Undissolved solid samples were assayed by XRPD to confirm crystallinity and to confirm crystal form did not change (i.e., no new polymorphs).

Figure 2:
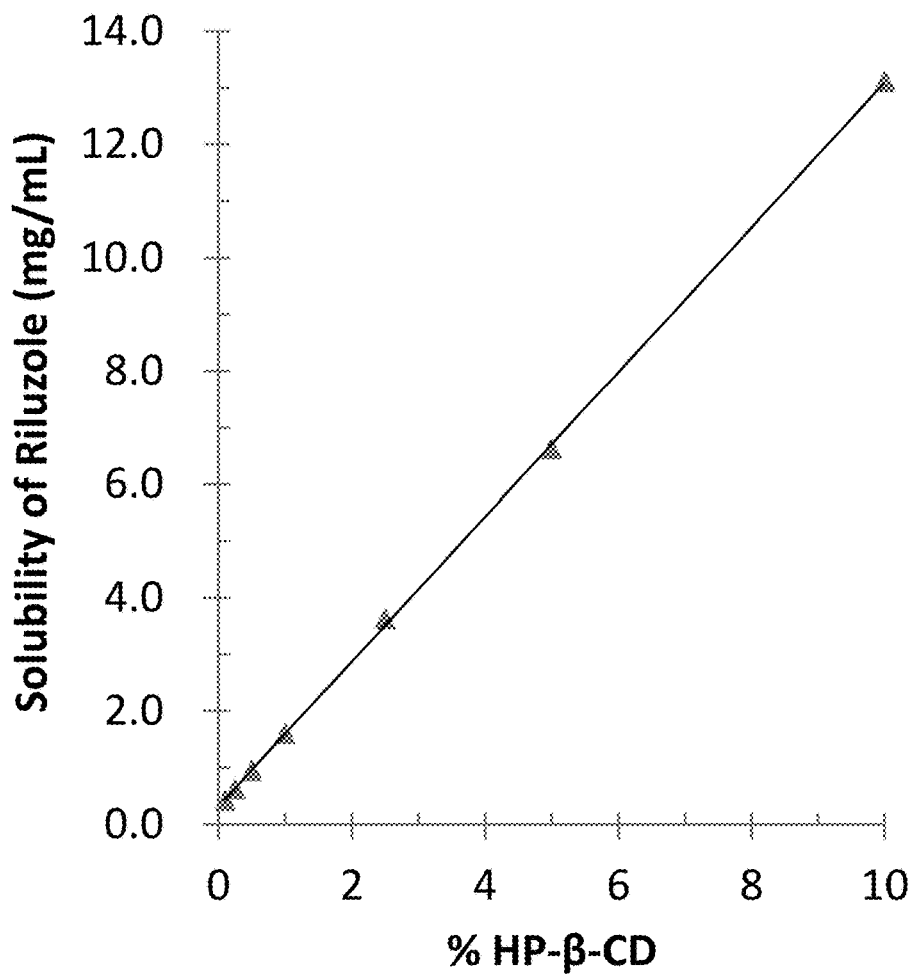
FIG. 2 depicts the solubility of riluzole in HP-β-CD at room temperature after 1 week. An appropriate amount of riluzole was added to aqueous solutions that contained 10%, 5%, 2.5%, 1%, 0.5%, 0.25%, and 0.1% HP-β-CD, all made isotonic with NaCl, to aqueous NaCl solution (9 mg/ml NaCl, normal saline), and to pure water. An appropriate excess amount of riluzole was added to each of the sample solution as needed to obtain saturated solutions of riluzole for HPLC analysis of Riluzole concentration, and to perform XRPD analysis on undissolved solid riluzole. Riluzole-containing sample suspensions were stirred at 500 rpm at room temperature. Supernatants were assayed after 48 hours of equilibration by HPLC for Riluzole concentration, and undissolved solid by XRPD for crystallinity and polymorphism.
Figure 3A:
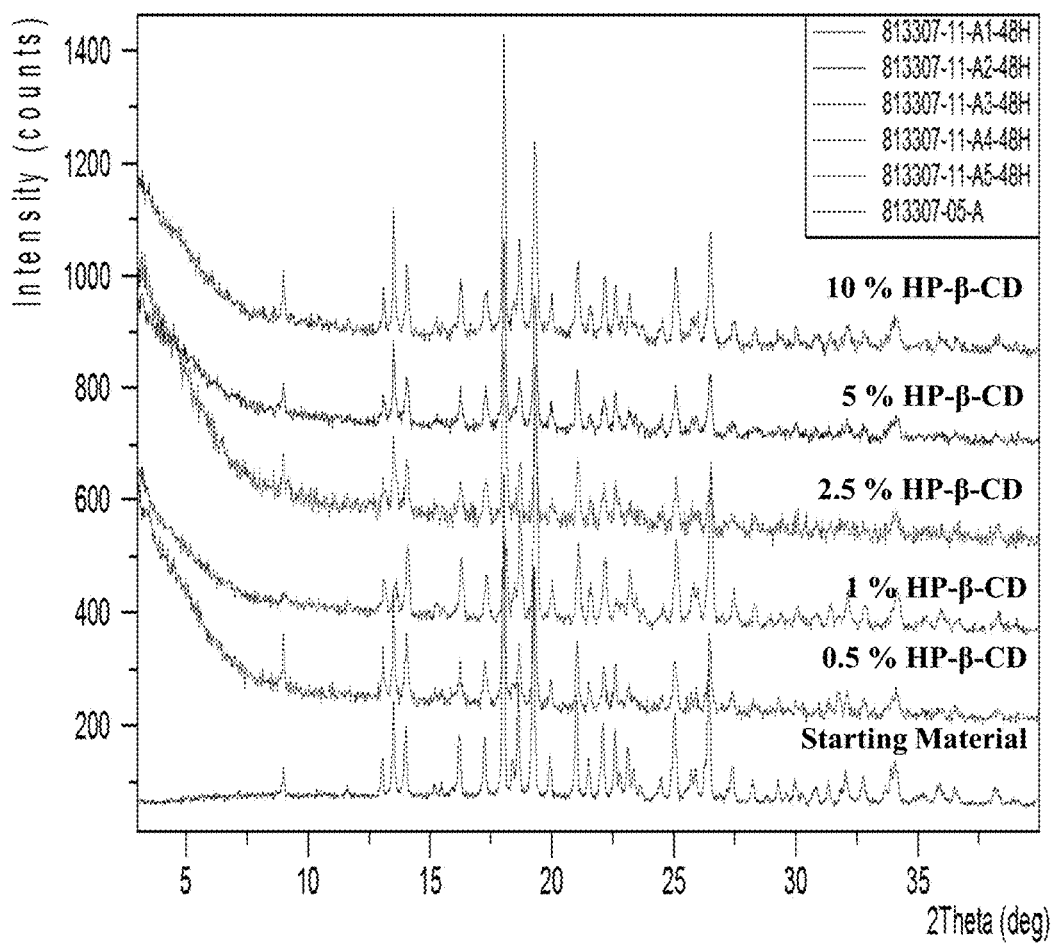
FIG. 3A-B depicts the XRPD patterns for residual solids recovered from riluzole solubility experiments that were conducted in HP-β-CD at room temperature after 48 hours. An appropriate amount of riluzole was added to aqueous solutions that contained 10%, 5%, 2.5%, 1%, 0.5%, 0.25%, and 0.1% HP-β-CD, all made isotonic with NaCl, to aqueous NaCl solution (9 mg/ml NaCl, normal saline), and to pure water. An appropriate excess amount of riluzole was added to each of the sample solution as needed to obtain saturated solutions of riluzole for HPLC analysis of Riluzole concentration, and to perform XRPD analysis on undissolved solid riluzole. Riluzole-containing sample suspensions were stirred at 500 rpm at room temperature. Supernatants were assayed after 48 hours of equilibration by HPLC for Riluzole concentration, and undissolved solid by XRPD for crystallinity and polymorphism
Figure 3B:
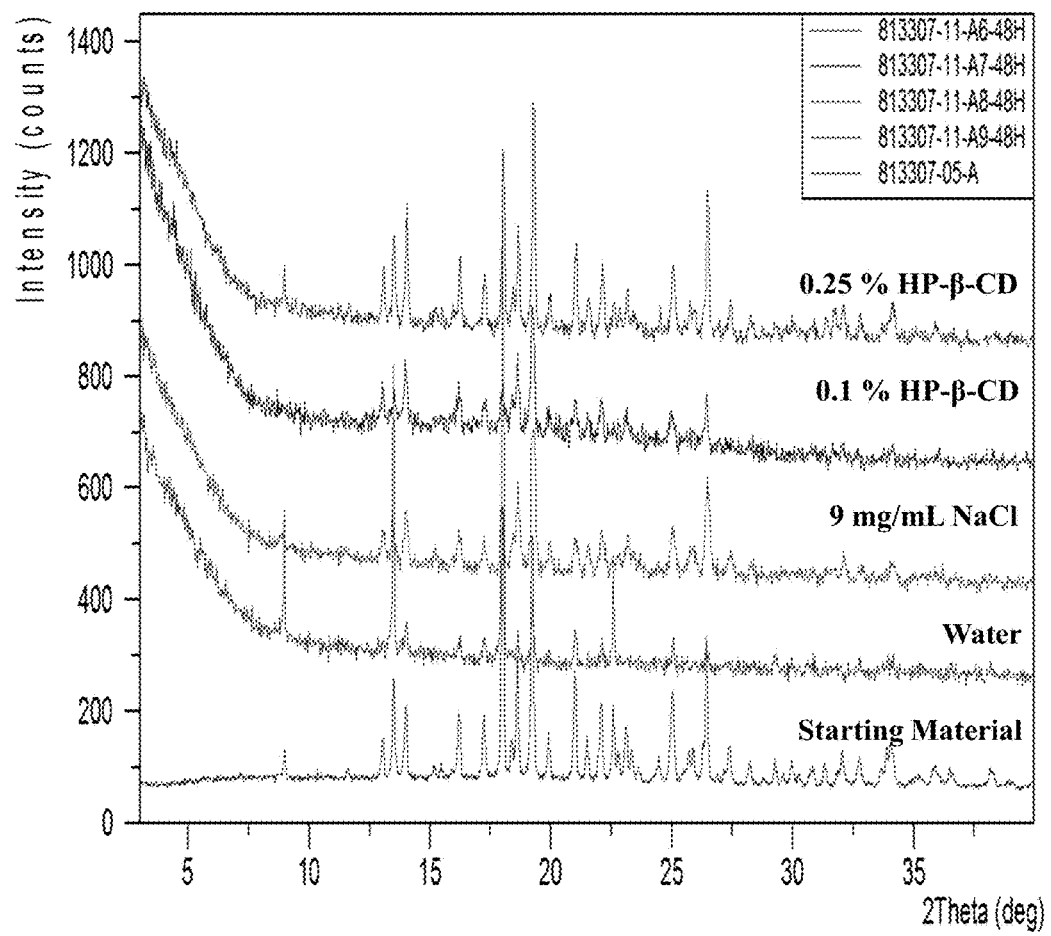
Figure 4A:
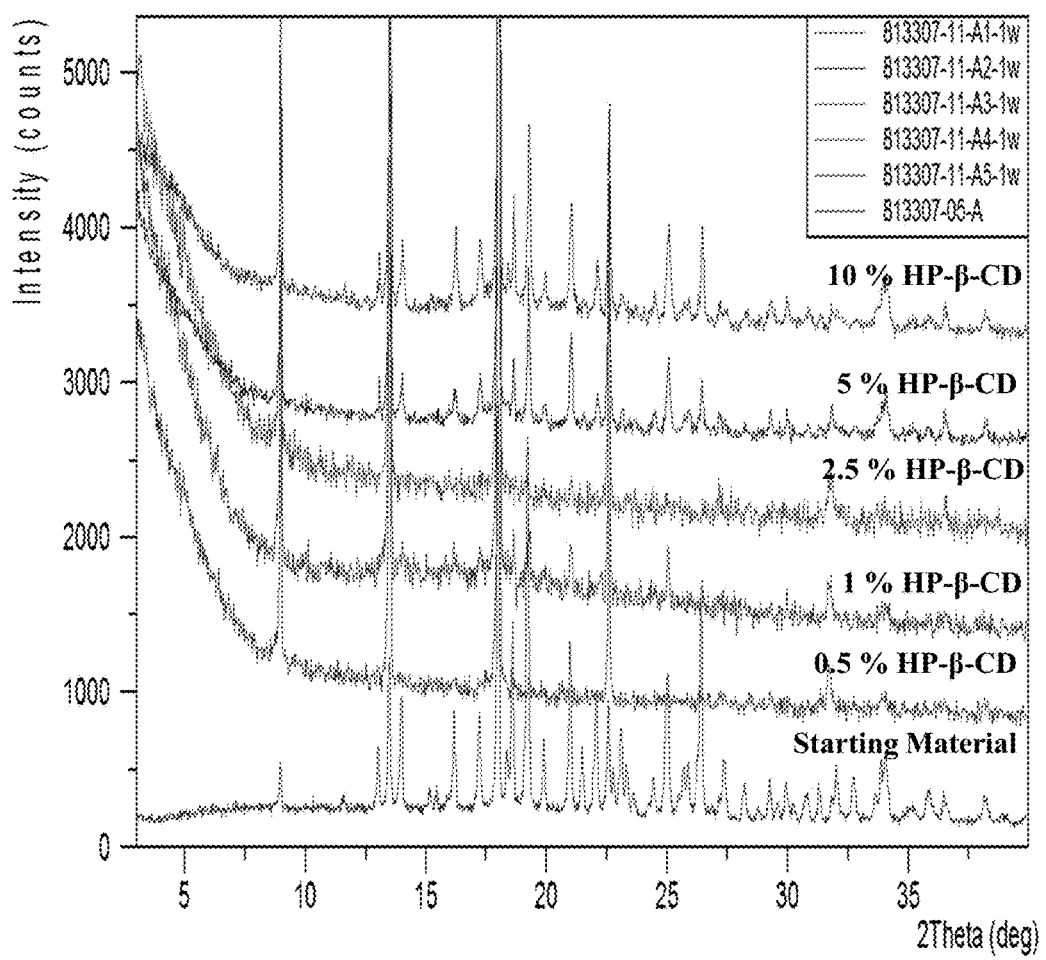
FIG. 4A-B depicts the XRPD patterns for residual solids recovered from riluzole solubility experiments that were conducted in HP-β-CD at room temperature after 1 week. An appropriate amount of riluzole was added to aqueous solutions that contained 10%, 5%, 2.5%, 1%, 0.5%, 0.25%, and 0.1% HP-β-CD, all made isotonic with NaCl, to aqueous NaCl solution (9 mg/ml NaCl, normal saline), and to pure water. An appropriate excess amount of riluzole was added to each of the sample solution as needed to obtain saturated solutions of riluzole for HPLC analysis of Riluzole concentration, and to perform XRPD analysis on undissolved solid riluzole. Riluzole-containing sample suspensions were stirred at 500 rpm at room temperature. Undissolved solids were assayed after 1 week of equilibration by XRPD for crystallinity and polymorphism.
Figure 4B:
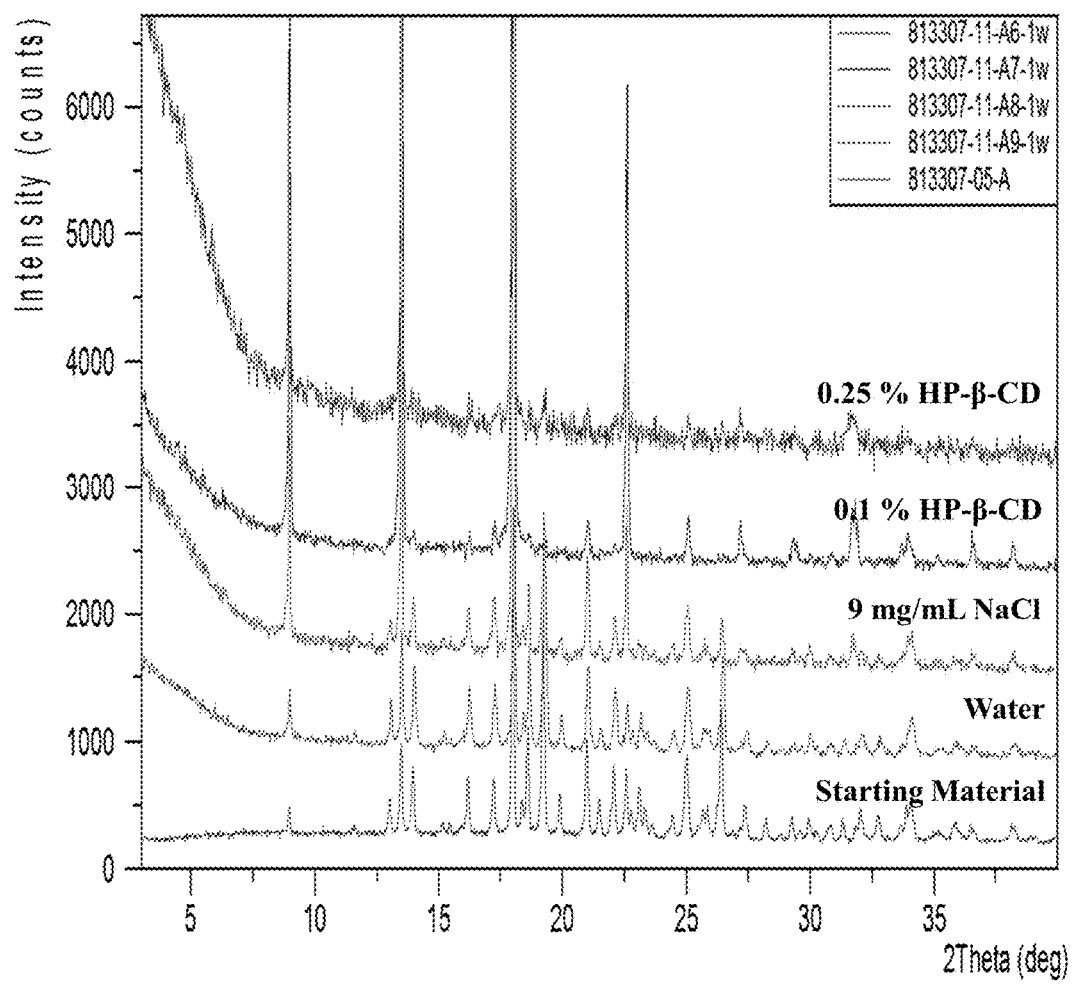

Data show that the solubility of riluzole increased linearly with the increasing concentration of HP-β-CD after 48 hours (FIG. 1) or 1 week (FIG. 2). Further, there was no crystal form change in riluzole at any concentration of HP-β-CD after 48 hours (FIG. 3A and FIG. 3B) or 1 week (FIG. 4A and FIG. 4B).

Figure 5:
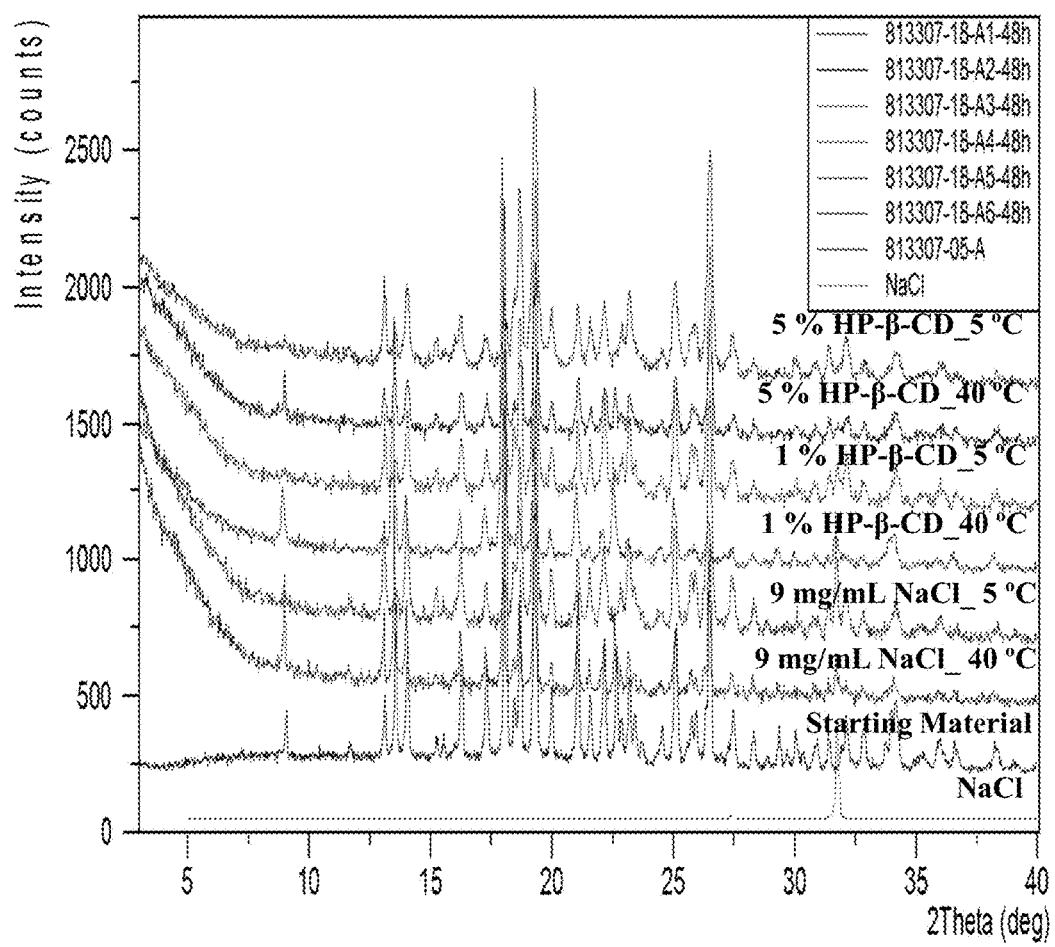
FIG. 5 depicts the XRPD patterns for residual solids recovered from riluzole solubility experiments that were conducted in 5% HP-β-CD and 1% HP-β-CD sample solutions at 5° C. and 40° C. for 48 hours. Solubility was also determined in solution B (9 mg/ml NaCl) and H₂O. An appropriate excess amount of riluzole was added to each of the sample solutions as needed to obtain saturated solutions of riluzole and perform XRPD on undissolved solid riluzole. Samples were assayed after 48 hours by XRPD.
Figure 6:
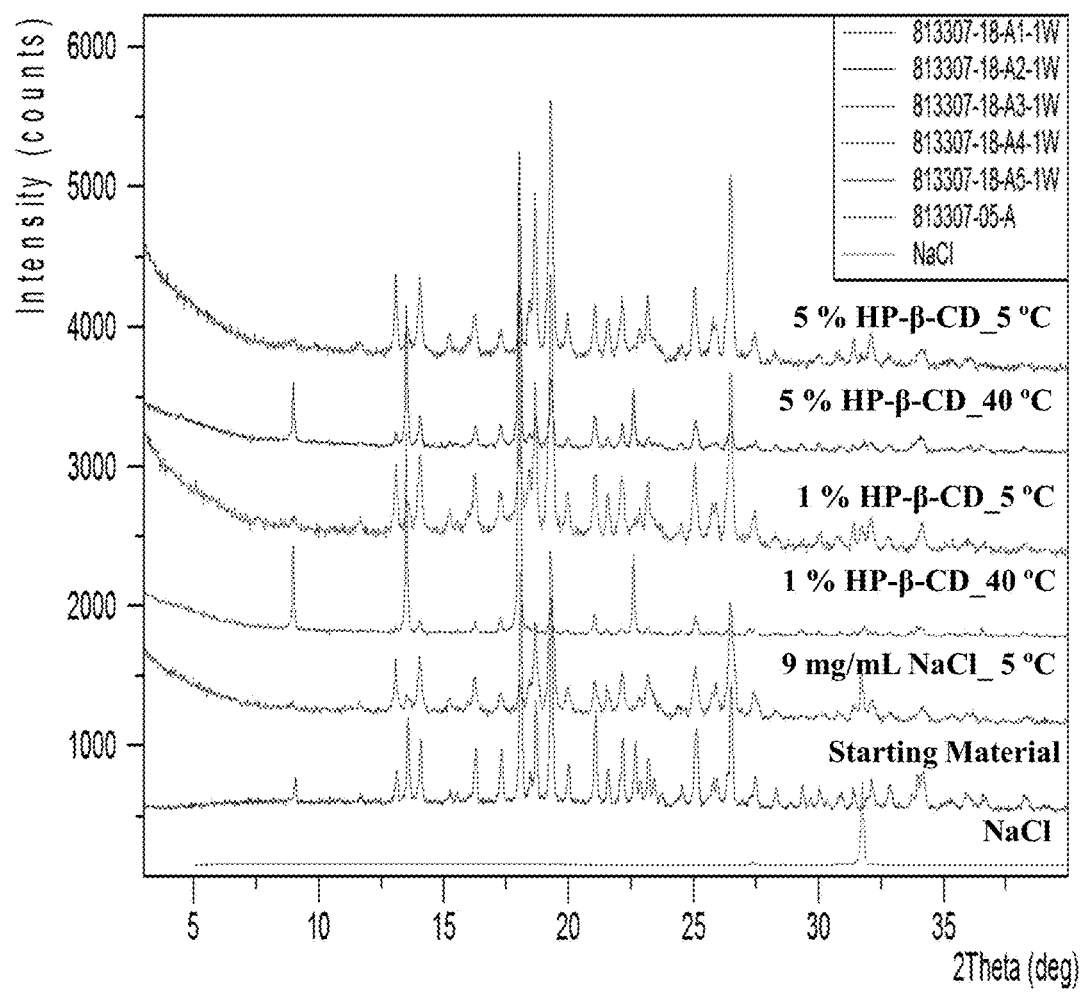
FIG. 6 depicts the XRPD patterns for residual solids recovered from riluzole solubility experiments that were conducted in 5% HP-β-CD and 1% HP-β-CD sample solutions at 5° C. and 40° C. for 1 week. Solubility was also determined in solution B (9 mg/ml NaCl) and H₂O. An appropriate excess amount of riluzole was added to each of the sample solutions as needed to obtain saturated solutions of riluzole and perform XRPD on undissolved solid riluzole. Samples were assayed after 1 week by XRPD.

Solubility of riluzole was determined in 5% HP-β-CD and 1% HP-β-CD sample solutions at 5° C. and 40° C. for 48 hours and 1 week. Stock solution B (9 mg/ml NaCl) and $H_2O$ were used as sample solution blanks. Solubility of riluzole at 5° C. and 40° C. was consistent with riluzole solubility at room temperature. No form change in riluzole occurred at any concentration of HP-β-CD after 48 hours (FIG. 5) or 1 week (FIG. 6).

Next, 1 mg/ml riluzole was added to three solutions, each containing 1% HP-β-CD, 0.8% NaCl and 5 mM sodium phosphate buffer, prior to adjusting the pH to 6.3, 7.2 and 7.9 respectively. Similarly, 5 mg/ml riluzole was added to three solutions, each containing 5.5% HP-β-CD, 0.65% NaCl and 5 mM sodium phosphate buffer, prior to adjusting the pH to 6.3, 7.2 and 7.9 respectively. All samples were placed in stability chambers maintained at either 5° C., 50° C. or 70° C. After all samples were incubated for 12 days at the respective temperatures, chemical stability was assed. All experimental solutions of riluzole showed good solution stability at 5° C., 50° C. or 70° C. after 12-day incubation (Table 1).

TABLE 1

| Riluzole (mg/ml) | Buffer | Temp. (° C.) | Assay (%) | Area of API (%) |
|---|---|---|---|---|
| 1 | 1% Trappsol ® HPBCD-EC + 0.8% NaCl + 5 mM sodium phosphate buffer (pH 6.3) | 5 | 98.9 | 100.00 |
| 1 | | 50 | 99.5 | 100.00 |
| 1 | | 70 | 97.6 | 100.00 |
| 1 | 1% Trappsol ® HPBCD-EC + 0.8% NaCl + 5 mM sodium phosphate buffer (pH 7.2) | 5 | 99.5 | 100.00 |
| 1 | | 50 | 101.5 | 100.00 |
| 1 | | 70 | 99.3 | 100.00 |
| 1 | 1% Trappsol ® HPBCD-EC + 0.8% NaCl + 5 mM sodium phosphate buffer (pH 7.9) | 5 | 99.2 | 100.00 |
| 1 | | 50 | 100.5 | 100.00 |
| 1 | | 70 | 98.9 | 100.00 |
| 5 | 5.5% Trappsol ® HPBCD-EC + 0.65% NaCl + 5 mM sodium phosphate buffer (pH 6.3) | 5 | 99.0 | 100.00 |
| 5 | | 50 | 99.6 | 100.00 |
| 5 | | 70 | 99.0 | 100.00 |
| 5 | 5.5% Trappsol ® HPBCD-EC + 0.65% NaCl + 5 mM sodium phosphate buffer (pH 7.2) | 5 | 99.1 | 100.00 |
| 5 | | 50 | 99.7 | 100.00 |
| 5 | | 70 | 98.6 | 100.00 |
| 5 | 5.5% Trappsol ® HPBCD-EC + 0.65% NaCl + 5 mM sodium phosphate buffer (pH 7.9) | 5 | 98.9 | 100.00 |
| 5 | | 50 | 99.6 | 100.00 |
| 5 | | 70 | 100.0 | 100.00 |

Nervous Tissue Accumulation.

Figure 7A:
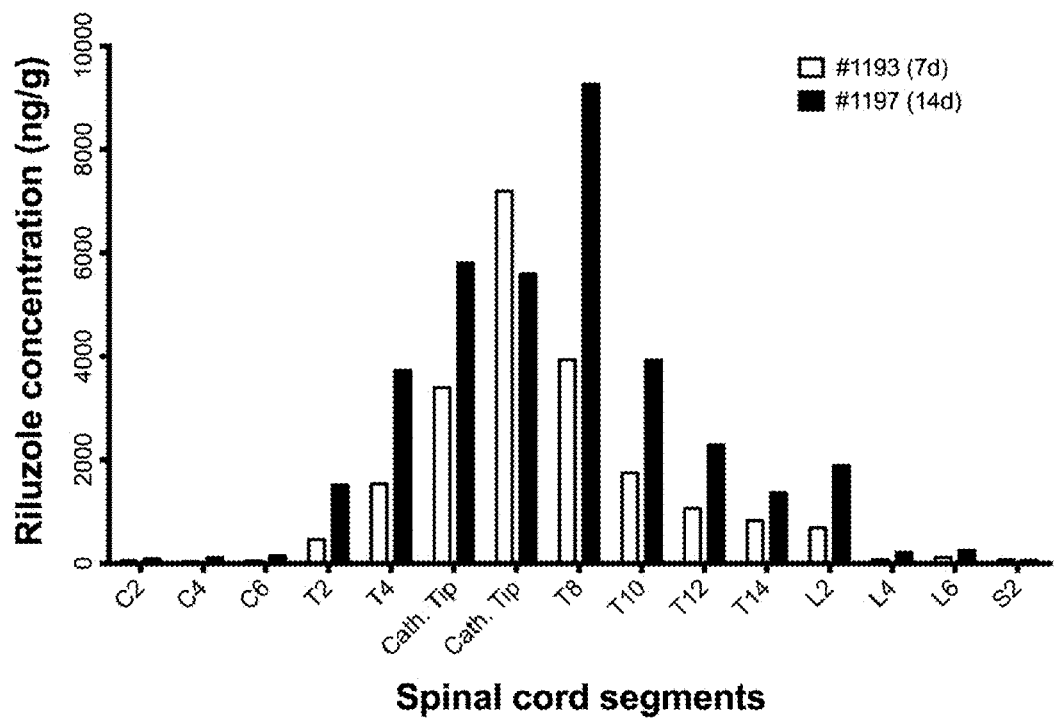
FIG. 7A-B depicts nervous tissue accumulation in two purpose-bred Mongrel dogs that received a continuous intrathecal (IT) infusion of riluzole (0.1 mg/hour) through a single catheter implanted between the T4 and T6 vertebrae. The animals were sacrificed after 7 or 14 days of riluzole treatment and a necropsy was immediately performed.
Figure 7B:
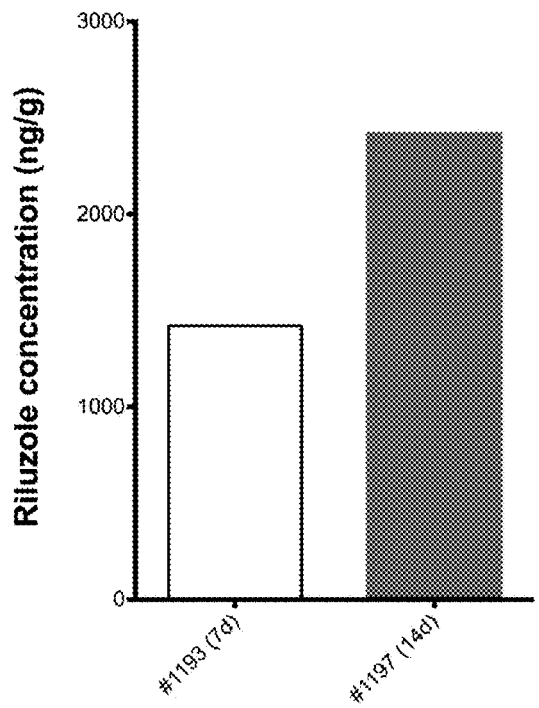

Two purpose-bred Mongrel dogs received a continuous intrathecal (IT) infusion of riluzole (0.1 mg/hour) through a single catheter implanted between the T4 and T6 vertebrae. Animals were sacrificed after 7 or 14 days of riluzole treatment and a necropsy was immediately performed. After 7 days, riluzole spread rostral and caudal to the catheter tip in the spinal cord (SC) and accumulated at levels greater than 1000 ng/g from the T4 vertebrae to the T12 vertebrae. After 14 days, riluzole accumulated at levels greater than 1000 ng/g from the T2 vertebrae to the L2 vertebrae (FIG. 7A). Total riluzole accumulation increased over time (FIG. 7B).

Figures 8A, 8B:
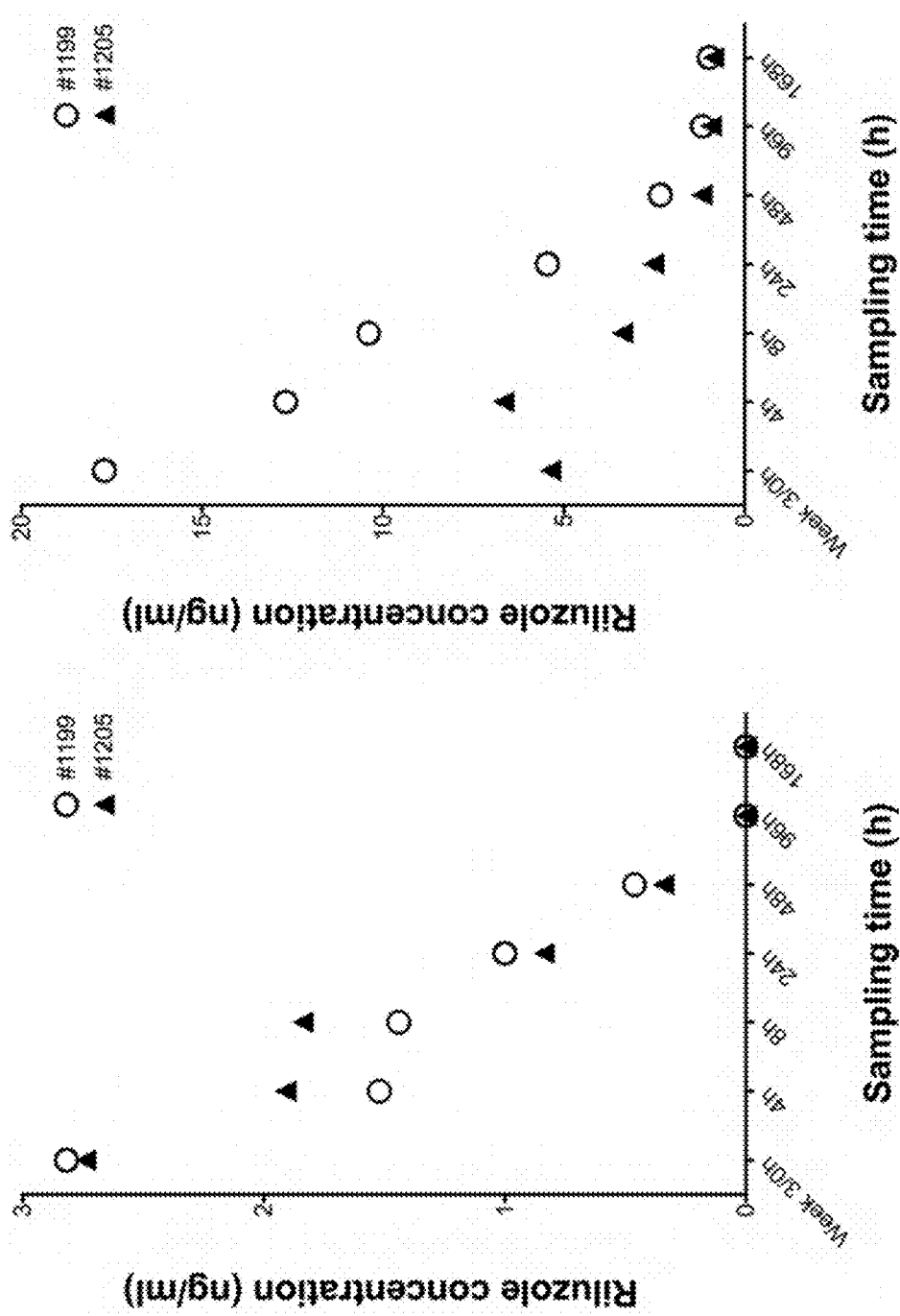
FIG. 8A-B depicts the fluids elimination profiles of riluzole from two purpose-bred Mongrel dogs (#1199 and #1205) that received a continuous IT infusion of riluzole (0.1 mg/hour) through a single catheter implanted between the T4 and T6 vertebrae for 3 weeks. After stopping the 3-week treatment, plasma and urine were collected at timed increments and riluzole levels were measured in the samples from dogs #1199 (white circles) and #1205 (black triangles).

In a separate study, two purpose-bred Mongrel dogs (#1199 and #1205) received a continuous IT infusion of riluzole (0.1 mg/hour) through a single catheter implanted between the T4 and T6 vertebrae for 3 weeks. After stopping the 3-week treatment, plasma and urine were collected at timed increments and riluzole levels were measured in the samples. The elimination half-life of riluzole from plasma was 12 hours and 14 hours for dogs #1199 and #1205, respectively (FIG. 8A). Riluzole was largely eliminated by the kidneys in urine (FIG. 8B).

Figures 9A, 9B:
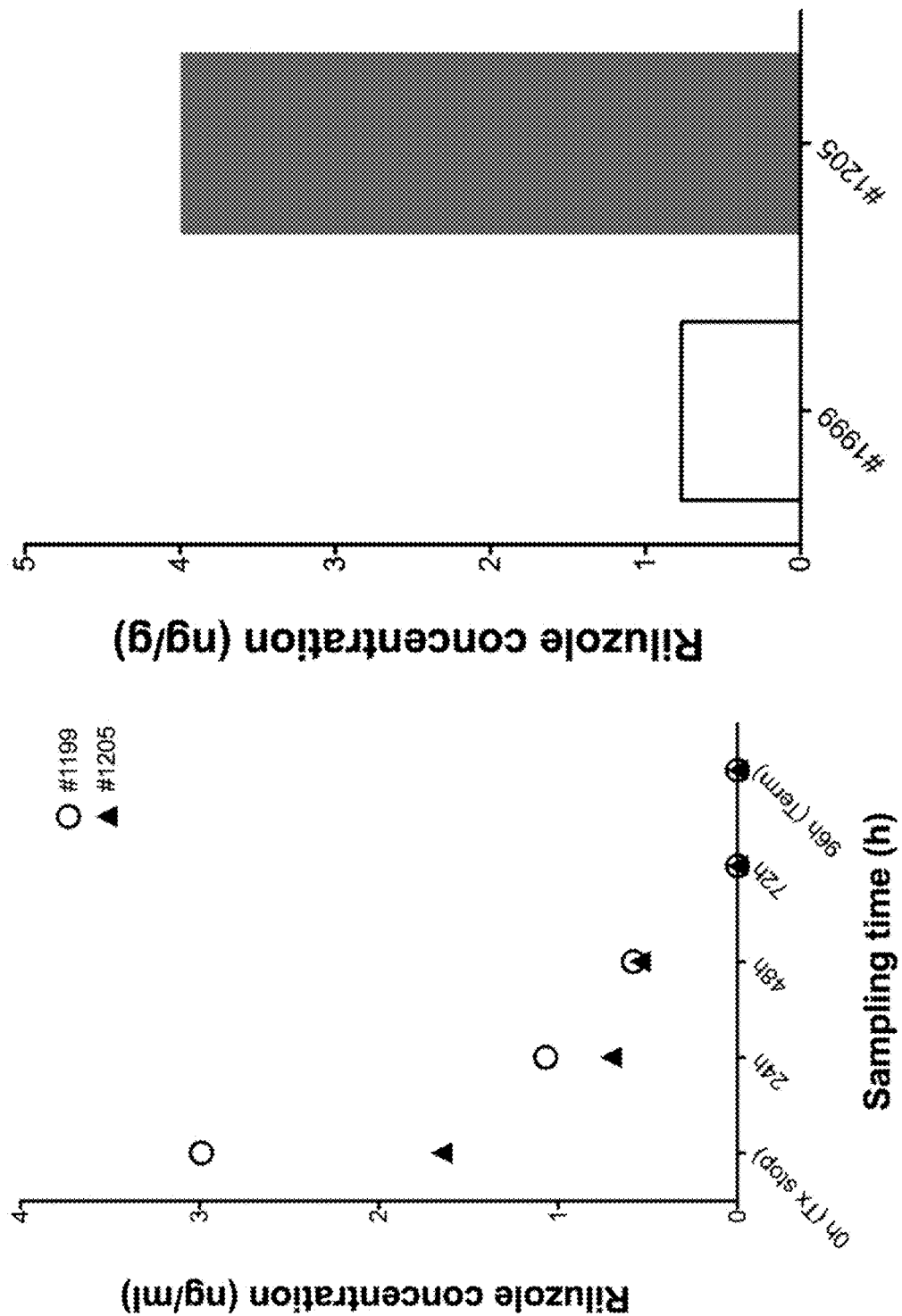
FIG. 9A-C depicts the CNS elimination profile of riluzole from dogs (#1199 and #1205). After a 3-week washout period, dogs #1199 (white bars) and #1205 (black bars) received an additional continuous IT infusion of riluzole (0.1 mg/hour) for 3 weeks. After treatment stop, plasma was collected at timed increments and riluzole levels were measured in the samples. 96 hours after treatment stop animals were sacrificed and a necropsy was immediately performed.
Figure 9C:
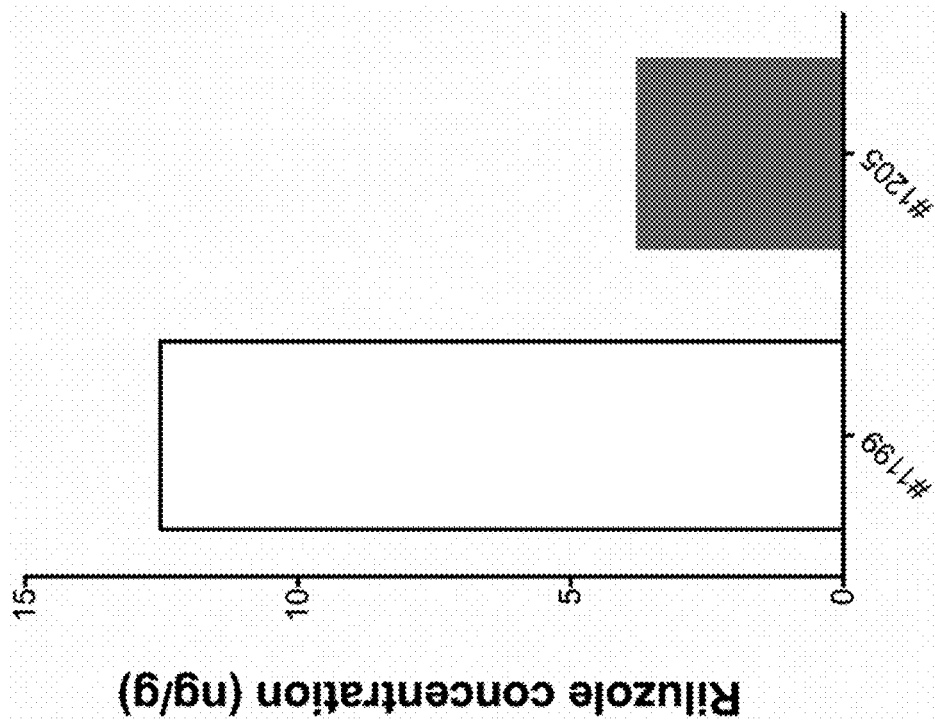

Three-week treated animals did not receive treatment for the following 3 weeks. After this 3-week washout period, dogs #1199 and #1205 received an additional continuous IT infusion of riluzole (0.1 mg/hour) for 3 weeks. After stopping the 3-weeks of additional riluzole treatment, plasma, urine, and CSF were collected at timed increments and riluzole levels were measured in the samples. 96 hours after treatment stop, animals were sacrificed and a necropsy was immediately performed. The elimination half-life of riluzole from plasma was 18 hours and 28 hours for dogs #1199 and #1205, respectively (FIG. 9A). Riluzole accumulation in brain tissue (FIG. 9B) and the spinal cord (FIG. 9C) was minimal (<15 ng/g) in both animals following the 96-hour washout period.

Dose Range Finding Studies.

Six purpose-bred Mongrel dogs received a continuous IT infusion of riluzole (0.25 mg/hour) through a single catheter implanted between the T4 and T6 vertebrae for 5 days. After stopping the 5-day treatment, plasma, urine, and CSF were collected and riluzole levels were measured in the samples. Animals were then sacrificed and a necropsy was immediately performed. In parallel, four Mongrel dogs received an oral administration of riluzole at a human equivalent dose of 2.6 mg/kg/day, given as twice-daily dosing (1.3 mg/kg BID) for 14 consecutive days. After stopping the 14-day treatment, one hour after the last pill administration, plasma, urine, and CSF were collected and riluzole levels were measured in the samples. Animals were then sacrificed and a necropsy was immediately performed.

Figure 10A:
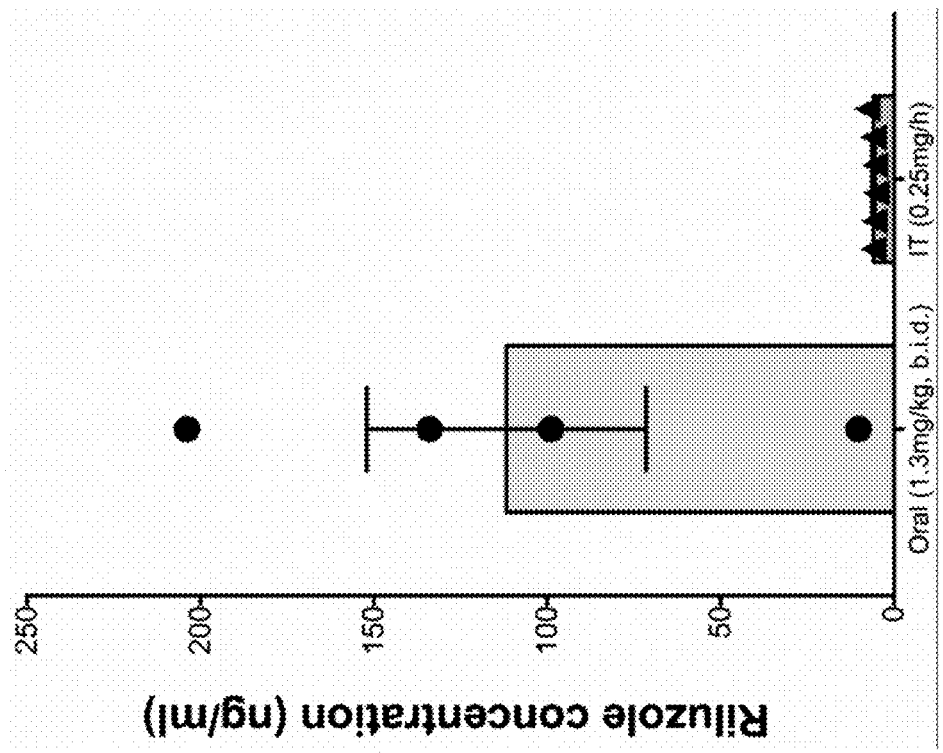
FIG. 10A-C depicts six purpose-bred Mongrel dogs that received a continuous IT infusion of riluzole (0.25 mg/hour) through a single catheter implanted between the T4 and T6 vertebrae for 5 days. After stopping the 5-day IT treatment, plasma, urine, and CSF were collected and riluzole levels were measured in the samples. Animals were then sacrificed and a necropsy was immediately performed. In parallel, four Mongrel dogs received an oral administration of riluzole at a human equivalent dose of 2.6 mg/kg/day, given as twice-daily dosing (1.3 mg/kg BID) for 14 consecutive days. After stopping the 14-day oral treatment, one hour after the last pill administration, plasma, urine, and CSF were collected and riluzole levels were measured in the samples.
Figures 10B, 10C:
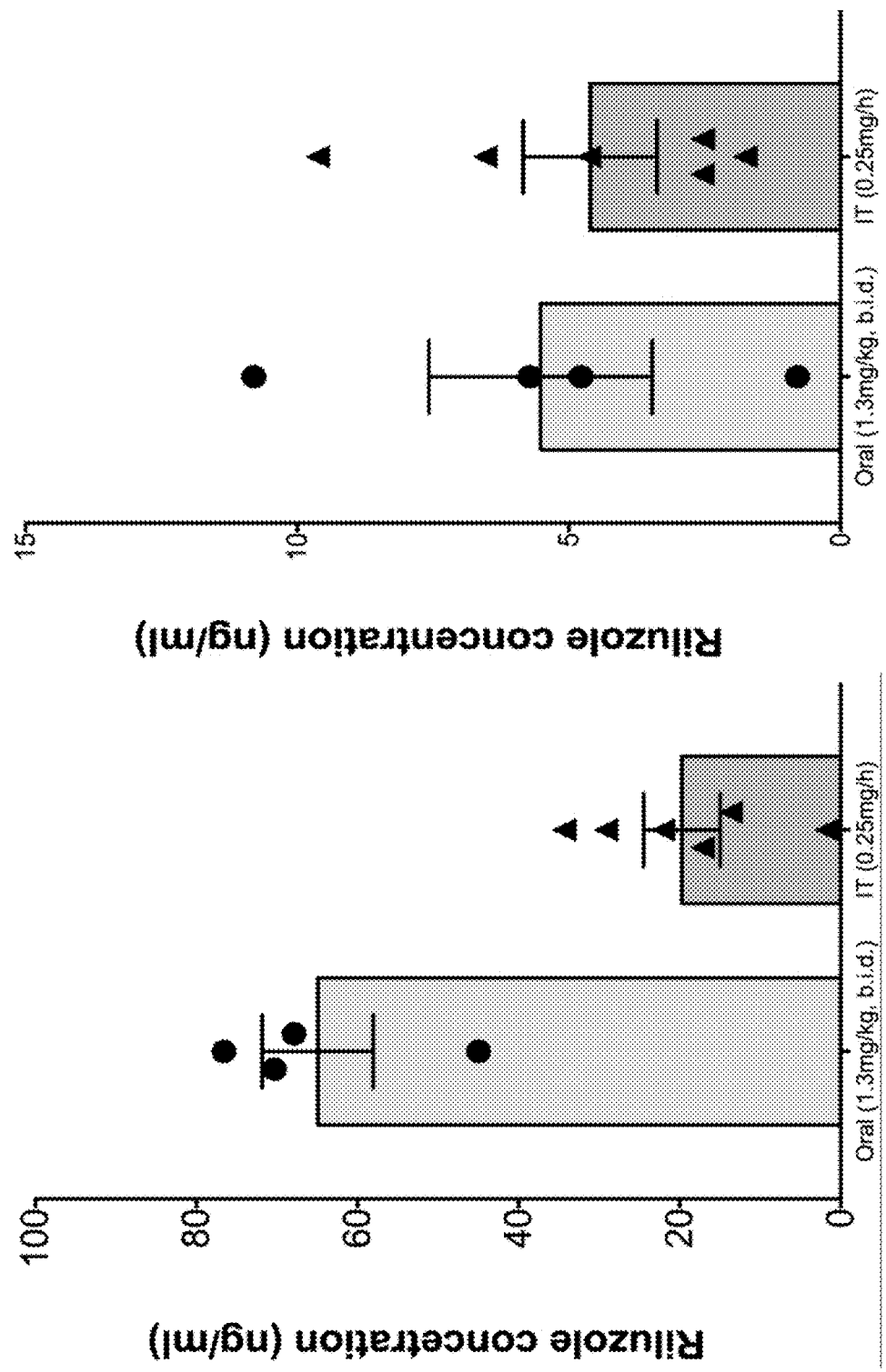
Figures 11A, 11B:
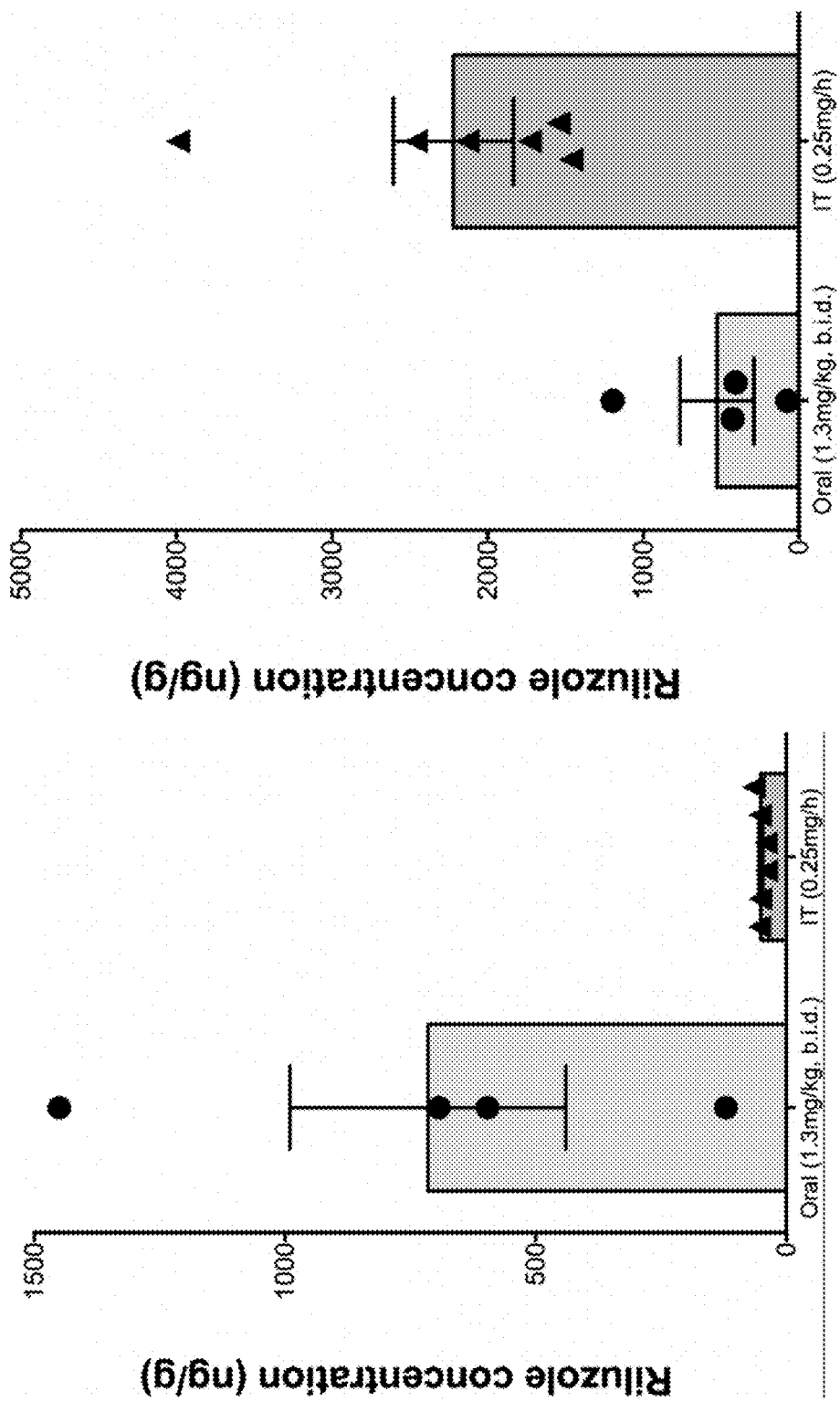
FIG. 11A-B depicts six purpose-bred Mongrel dogs that received a continuous IT infusion of riluzole (0.25 mg/hour) through a single catheter implanted between the T4 and T6 vertebrae for 5 days. After stopping the 5-day treatment, animals were sacrificed and a necropsy was immediately performed. In parallel four Mongrel dogs received an oral administration of riluzole at a human equivalent dose of 2.6 mg/kg/day, given as twice-daily dosing (1.3 mg/kg BID) for 14 consecutive days. One hour after stopping the 14-day treatment, animals were sacrificed and a necropsy was immediately performed.

Riluzole levels in plasma collected from 14-day, oral-treated dogs was approximately 20-fold higher compared to levels in plasma from 5-day, IT-treated dogs (FIG. 10A). Riluzole levels in urine collected from 14-day, oral-treated dogs was approximately 3-fold higher compared to levels in urine from 5-day, IT-treated dogs (FIG. 10B). Riluzole levels in CSF collected from 14-day, oral-treated dogs was similar to levels in CSF from 5-day, IT-treated dogs (FIG. 10C). Riluzole accumulation in brain tissue was approximately 700-fold higher in 14-day, oral-treated dogs compared to brain tissue of 5-day, IT-treated dogs (FIG. 11A). However, riluzole accumulation in the spinal cord was approximately 4-fold higher in 5-day, IT-treated dogs compared to spinal cord tissue harvested from 14-day, oral-treated dogs (FIG. 11B).

Example 2. Riluzole Formulation

In one embodiment, riluzole is formulated for intrathecal administration as follows.
Composition:

| Ingredient | Concentration | Amount for 100 ml |
|---|---|---|
| Riluzole | 4 mg/ml | 400 mg |
| Trappsol ® HPBCD-EC | 40 mg/ml | 4000 mg |
| Sodium chloride, USP | 7.5 mg/ml | 750 mg |
| Sodium Phosphate Dibasic Anhydrous, USP | 0.142 mg/ml (1 mM) | 14.2 mg |
| 0.1 N HCl and/or 0.1 N NaOH | qs. pH 7.40 | qs. pH 7.40 |
| WFI (water for injection) | qs. 1 ml | qs. 100 ml |

Procedure:
1. Add 25 ml of water for injection to a 200 ml beaker and initiate stirring.
2. Dissolve 14.2 mg of Dibasic Sodium Phosphate.
3. Dissolve 750 milligrams of sodium chloride.
4. Adjust the pH to 7.4 with 0.1 N HCl.
5. Add 4000 milligrams of Trappsol® HPBCD-EC and allow it to dissolve.

6. Add 400 milligrams of riluzole and allow it to dissolve.
7. Add 65 ml of water for injection.
8. Adjust pH to 7.40 if necessary with 0.01 N HCl or 0.01 N NaOH, whichever is needed.
9. Quantitatively transfer the solution from beaker to volumetric flask. Rinse the beaker twice consecutively with 4 ml with WFI and use rinses to make the volume to exactly 100 ml.

Example 3. Riluzole Formulation

In one embodiment, riluzole is formulated for intrathecal administration as follows.
Composition:

| Ingredient | Concentration | Amount for 10 liters* |
|---|---|---|
| Rlluzole | 4.00 mg/ml | 40.0 grams |
| Trappsol ® HPBCD-EC | 40.0 mg/ml | 400 grams |
| Sodium Phosphate Monobasic, Monohydrate, USP | 7.20 mg/ml | 72.0 grams |
| Sodium Phosphate Dibasic, Anhydrous, USP | 0.30 mg/ml (2.2 mM) | 3.00 grams |
| 0.1 N HCl and/or 0.1 N NaOH | 0.40 mg/ml (2.8 mM) | 4.00 grams |
| WFI (water for injection) | qs. pH 7.30 | qs. pH 7.30 |

*Formulation density = 1.016 g/ml

Procedure:
1. Tare a 4 L beaker and charge it with 2.0 kg of WFI.
2. Initiate gentle stirring with magnetic stir bar.
3. Add:
    3.00 grams of Sodium Phosphate Monobasic, Monohydrate
    4.00 grams of Sodium Phosphate Dibasic, Anhydrous
    72.0 grams of NaCl
    400 grams of Trappsol® HPBCD-EC
4. Allow all solid components to dissolve. Increase stirring speed if needed.
5. Add 40.0 grams of riluzole and allow it to dissolve. (This may take several hours.)
6. Tare a 5 gallon Nalgene tank and charge it with 3.0 kg of WFI.
7. Pour the contents of the 4 L Beaker from step 5 (except the stir bar) into the tank.
8. Rinse the inside of the 4 L beaker a minimum of 3 times with 1 liter of WFI, each time pouring the rinsing into the Nalgene tank.
9. Q.S. the solution using WFI to 9.50+/−0.02 kg.
10. Initiate mixing with mechanical stirrer.
11. While mixing, adjust the pH of the solution to 7.30. Use the 1N HCl to adjust the pH down or the 1N NaOH to adjust the pH up.
12. Mix the solution for a minimum of 15 minutes or until the solution is uniform, whichever is longer.
13. Q.S. the solution to 10.16 kg with WFI.
14. Check the pH. If pH is outside 7.25-7.35 range use the 1N HCl to adjust the pH down, or the 1N NaOH to adjust the pH up.
15. Sterile filter into an appropriate sterile receiving vessel.
16. Under aseptic conditions, fill the formulation into sterile vials, stopper and cap vials.

Example 4. Riluzole Formulation

In one embodiment, riluzole is formulated for intrathecal administration as follows:
Composition:

| Ingredient | Quantity |
|---|---|
| Rlluzole | 4 mg/ml |
| Trappsol ® EC | 40 mg/ml |
| Sodium Phosphate Dibasic Anhydrous, USP | 0.71 mg/ml |
| Sodium chloride, USP | 7.20 mg/ml |
| 0.1 N HCl | qs. pH 7.30 |
| WFI (water for injection) | qs. 1 ml |

Procedure for 10-Liter Batch Compounding:
1. Tare a 4 L beaker and charge it with 2.0 kg of WFI.
2. Initiate gentle stirring with magnetic stir bar.
3. Add 7.10 grams of Sodium Phosphate Dibasic, Anhydrous
4. Add 72.0 grams of NaCl
5. Adjust pH to 6-9 (preferably 7.5-8.5). Use 1N HCl to adjust the pH down, or 1N NaOH to adjust the pH up.
6. Add 400 grams of Trappsol® EC
7. Add 40.0 grams of riluzole.
8. Allow all solid components to dissolve. Increase stirring speed if needed. (This may take several hours.)
9. Tare a 5 gallon Nalgene tank and charge it with 3.0 kg of WFI.
10. Pour the contents of the 4 L Beaker from step 8 (except the stir bar) into the tank.
11. Rinse the inside of the 4 L beaker a minimum of 3 times with 1 liter of WFI, each time pouring the rinsing into the Nalgene tank.
12. Q.S. the solution using WFI to 9.50+/−0.02 kg.
13. Initiate mixing with mechanical stirrer.
14. Mix the solution for a minimum of 15 minutes or until the solution is uniform, whichever is longer.
15. While mixing, adjust the pH of the solution to 7.30. Use the 1N HCl to adjust the pH down or the 1N NaOH to adjust the pH up.
16. Q.S. the solution to 10.16 kg with WFI.
17. Check the pH. If pH is outside 7.25-7.35 range use 1N HCl to adjust the pH down, or 1N NaOH to adjust the pH up.
18. Sterile filter into an appropriate sterile receiving vessel.
19. Under aseptic conditions, fill the formulation into sterile vials, stopper and cap vials.

Example 5. Combination Treatment with IT Riluzole and Oral Riluzole

To determine the tolerability and pharmacokinetics of a combination of a dose of intrathecal (IT) and oral riluzole, four male mixed breed hound dogs were surgically implanted with an intrathecal catheter and were administered riluzole by a continuous 24 hour infusion over five days (Days 0 to 5) at a dose level of 0.2 mg/hour and also by one 50 mg oral tablet twice daily (every 12±4 hours) on Days 0 to 4 and once on Day 5 which was approximately equal to a dose level of 1.8 to 2.1 mg/kg/dose. To prepare the intrathecal formulation, the appropriate amount of vehicle (5% Trappsol® HPBCD-EC in 0.9% Sodium Chloride for Injection, USP) was mixed with the appropriate amount of riluzole powder at a nominal concentration of 3.64 mg/mL. The intrathecal formulation was prepared on the day prior to infusion and was filtered through a 0.22 micron PVDF and stored at room temperature. The IT formulation was administered at a programmed infusion rate of 1.32 mL/day (i.e.

0.2 mg/hour). The riluzole tablets were dispensed prior to dosing and were stored at room temperature.

Observations for morbidity, mortality, injury, and the availability of food and water were conducted twice daily for all animals. Clinical observations were conducted daily. Canine behavioral testing to assess muscle tone, motor coordination, and state of arousal was conducted daily beginning on Day 10. Neurological evaluations were conducted pretest, Day 1, and prior to necropsy. Body weights were measured and recorded on Day −1 and 4. Physical examinations were conducted pretest, Day −1, and prior to necropsy. Blood, urine, and cerebrospinal fluid (CSF) samples were collected pretest, prior to necropsy, and at necropsy. At study termination, necropsy examinations were performed, and designated tissues were collected and preserved for possible future microscopic and bioanalytical analyses.

The results of this study demonstrated that continuous intrathecal infusion of the test article at a dose of 0.20 mg/hr paired with twice daily oral riluzole for five days was not associated with any mortality, clinical findings, body weight changes, motor or neurologic deficits, or macroscopic observations. Intrathecal infusion of riluzole paired with oral administration of riluzole for 5 days resulted in good biodistribution throughout the spinal cord with highest levels of riluzole in the tissue centered around the catheter tip and decreasing levels more distal from the infusion site (FIG. 12B). Riluzole was also found throughout the brain.

Figure 12A:
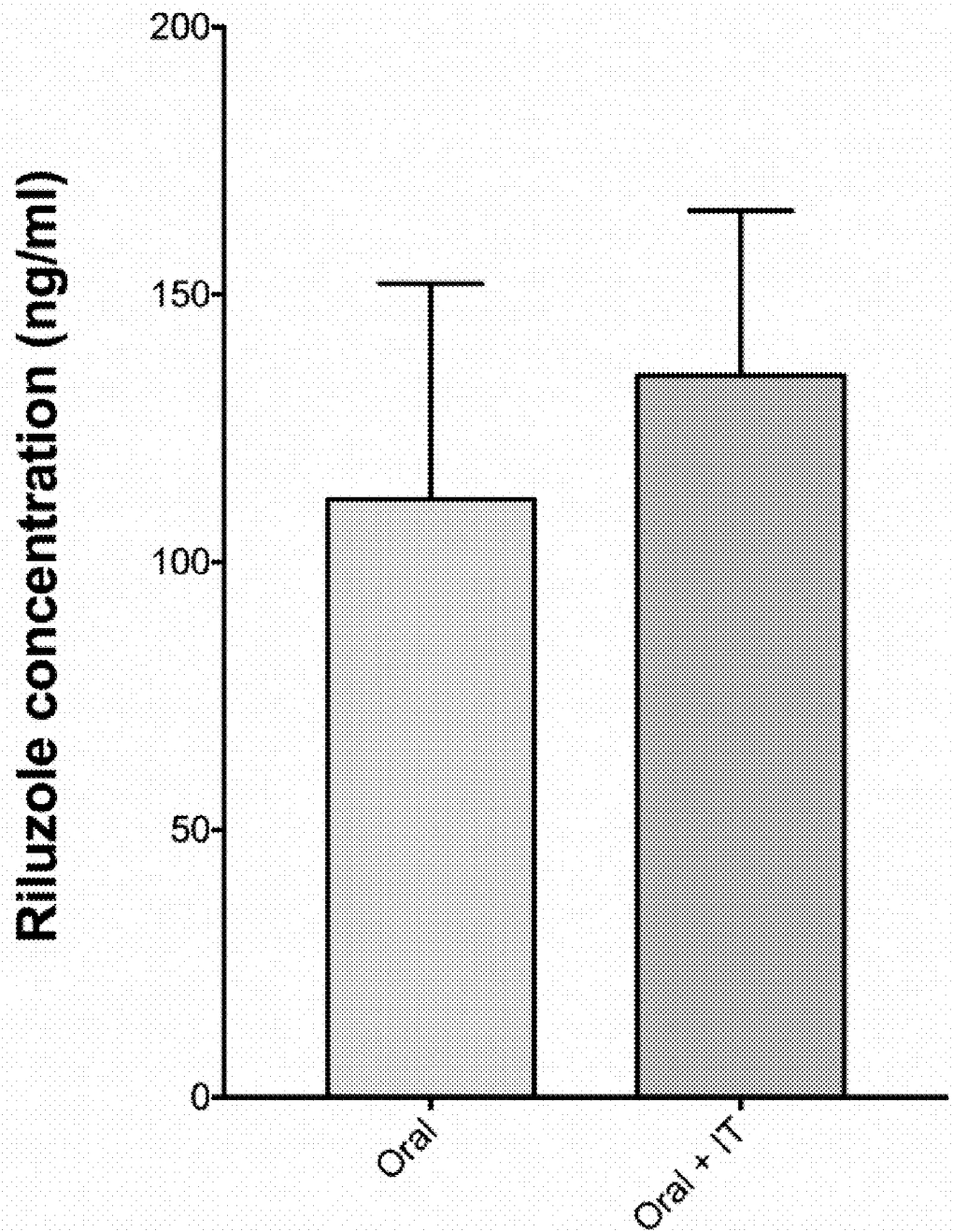
FIG. 12A-B shows a comparison of the fluids and tissue concentration of riluzole after oral administration alone or in combination with IT delivery.
Figure 12B:
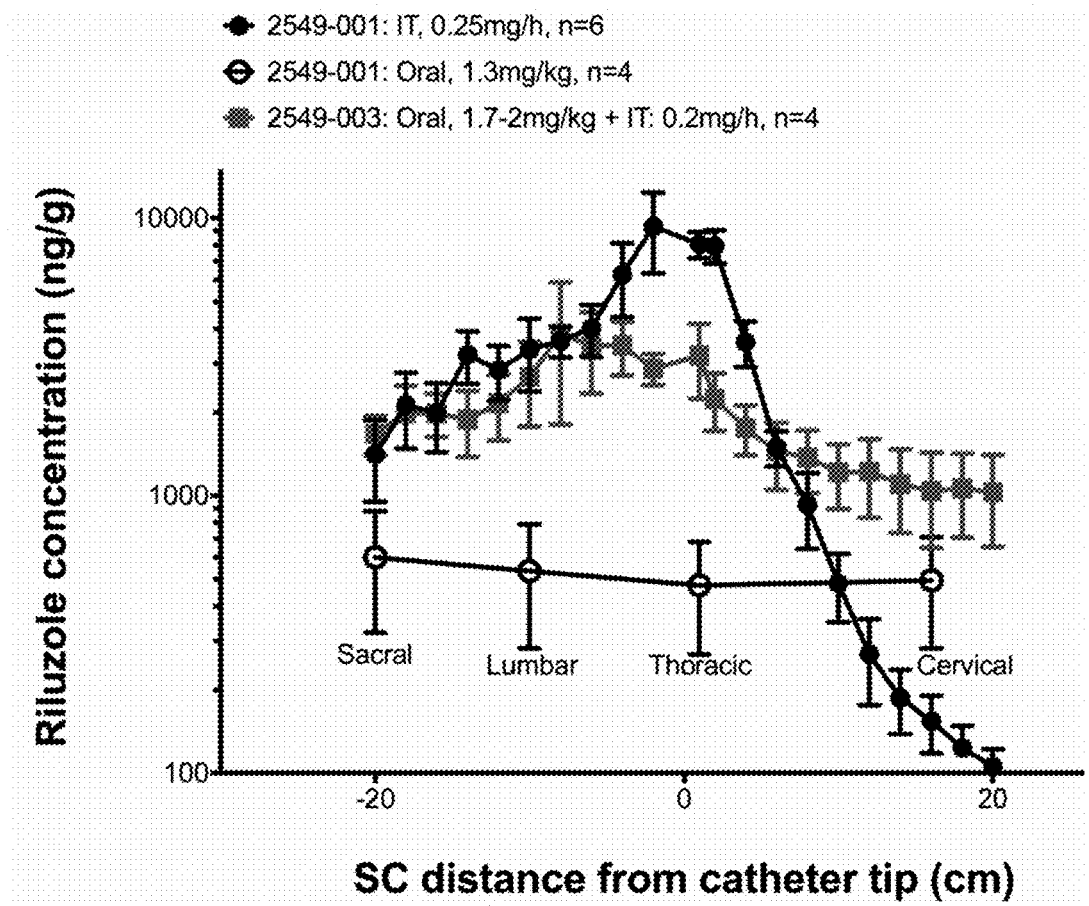

A comparison of the data from this study to data from the dose range finding study described in Example 1 is provided in FIG. 12. The dose range finding study included a comparison between IT riluzole at 0.25 mg/hour over a 5 day IT infusion period and oral riluzole equivalent to 50 mg BID in humans. As shown in FIG. 12A, a combination dose of oral and IT riluzole did not substantially increase the amount of riluzole measured in the plasma as compared to an oral dose alone. FIG. 12B shows that higher concentrations of riluzole are achieved in the spinal cord by IT administration as compared to oral administration, and combining oral riluzole with IT riluzole appeared to have an additive effect.

Overall, the results of this study have established that a 5 day continuous intrathecal infusion of 0.2 mg/hr of riluzole paired with twice daily oral administration of 50 mg of riluzole is well tolerated. In addition, the combination dose does not substantially increase the amount of riluzole measured in plasma samples, while providing greater spinal cord concentrations than oral administration alone.

What is claimed is:

1. A method for treating a subject in need thereof, the method comprising parenterally administering to the subject riluzole at a dose that is less than 10 mg per day and further administering riluzole orally at 50 mg twice a day.

2. The method of claim 1, wherein the parenterally administered daily dose is about 0.4 mg to about 9.5 mg or about 0.4 mg to about 7.5 mg.

3. The method of claim 1, wherein the parenterally administered daily dose is about 0.4 mg to about 5 mg.

4. The method of claim 1, wherein the parenterally administered daily dose is about 0.4 mg to about 4 mg.

5. The method of claim 1, wherein the parenterally administered daily dose is about 0.1 mg to about 4 mg.

6. The method of claim 1, wherein the parenterally administered daily dose is about 1 mg to about 4 mg.

7. The method of claim 1, wherein the parenterally administered riluzole is injected or infused into the subject's brain, spinal cord, or a cerebral ventricle.

8. The method of claim 1, wherein the parenterally administered riluzole is intrathecally administered and, optionally, wherein administration occurs continuously.

9. The method of claim 7, wherein parenteral administration does not result in a substantial increase in serum AUC of riluzole or a metabolite thereof.

10. The method of claim 1, wherein the parenterally administered riluzole is formulated as a composition comprising about 0.4 mg to about 10 mg per ml of riluzole dissolved in at least 1% (w/v) ß-cyclodextrin and an aqueous solvent, and wherein the composition a pH of about 5 to about 8.

11. The method of claim 10, wherein the parenterally administered riluzole composition comprises about 0.4 mg to about 10 mg per ml of riluzole dissolved in about 1% (w/v) to about 15% (w/v) ß-cyclodextrin and an aqueous solvent.

12. The method of claim 10, wherein the parenterally administered riluzole composition comprises about 0.4 mg to about 10 mg per ml of riluzole dissolved in about 1% (w/v) to about 10% (w/v) ß-cyclodextrin and an aqueous solvent.

13. The method of claim 10, wherein the parenterally administered riluzole composition comprises about 0.4 mg to about 4 mg per ml of riluzole dissolved in about 1% (w/v) to about 5% (w/v) ß-cyclodextrin and an aqueous solvent.

14. The method of any one of claim 10, wherein the parenterally administered riluzole composition further comprises one or more pharmaceutically acceptable excipient and/or one or more additional active ingredient.

15. The method of claim 10, wherein the ß-cyclodextrin is selected from the group consisting of 2,6-di-O-methyl-ß-cyclodextrin, 2-hydroxypropyl-ß-cyclodextrin, and sulfobutylether ß-cyclodextrin.

16. The method of claim 10, wherein the aqueous solvent is water, saline, or dextrose.

17. The method of claim 1, wherein treatment alleviates one or more symptoms in the subject, delays progression of a disease in the subject, slows progression of a disease in the subject, or extends survival of the subject.

18. The method of claim 1, wherein the subject in need of treatment with riluzole is a subject with motor neuron disease, spinal muscular atrophy, spinal cord injury, Parkinson's disease, Multiple Sclerosis, Alzheimer's disease, depression, Tourette Syndrome, general anxiety disorders, schizophrenia, or bipolar disorder.

19. The method of claim 18, wherein the subject in need of treatment with riluzole is a subject with amyotrophic lateral sclerosis.

* * * * *